United States Patent
Bertozzi et al.

(10) Patent No.: US 11,041,850 B2
(45) Date of Patent: Jun. 22, 2021

(54) METHOD FOR DETECTING PROTEIN-SPECIFIC GLYCOSYLATION

(71) Applicant: The Regents of the University of California, Oakland, CA (US)

(72) Inventors: Carolyn R. Bertozzi, Stanford, CA (US); Peter V. Robinson, Berkeley, CA (US); Cheng-Ting Tsai, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 275 days.

(21) Appl. No.: 15/741,728

(22) PCT Filed: Jul. 6, 2016

(86) PCT No.: PCT/US2016/041185
§ 371 (c)(1),
(2) Date: Jan. 3, 2018

(87) PCT Pub. No.: WO2017/007847
PCT Pub. Date: Jan. 12, 2017

(65) Prior Publication Data
US 2018/0203000 A1    Jul. 19, 2018

Related U.S. Application Data

(60) Provisional application No. 62/189,630, filed on Jul. 7, 2015.

(51) Int. Cl.
*G01N 33/532* (2006.01)
*C12Q 1/6876* (2018.01)
*C12Q 1/68* (2018.01)

(52) U.S. Cl.
CPC ............ *G01N 33/532* (2013.01); *C12Q 1/68* (2013.01); *C12Q 1/6876* (2013.01);
(Continued)

(58) Field of Classification Search
None
See application file for complete search history.

(56) References Cited

U.S. PATENT DOCUMENTS

2004/0023207 A1* 2/2004 Polansky ............... A61K 31/00
435/5
2007/0134665 A1 6/2007 Dellaire et al.
(Continued)

FOREIGN PATENT DOCUMENTS

WO  WO 2014/006123   1/2014
WO  WO 2014/145458   9/2014
WO  WO 2014/207245   12/2014

OTHER PUBLICATIONS

Gao et al. Method for Cellular Imaging of Palmitoylated Proteins with Clickable Probes and Proximity Ligation Applied to Hedgehog, Tubulin, and Ras. Journal of the American Chemical Society 136:4544-4550. (Year: 2014).*
Gullberg et al. Visualization and quantification of protein-protein interactions in cells and tissues. Nature Methods 7(6):v-vi. (Year: 2010).*
Soderberg et al. Direct observation of individual endogenous protein complexes in situ by proximity ligation. Nature Methods 3(12): 995-1000. (Year: 2006).*
(Continued)

*Primary Examiner* — Samuel C Woolwine
(74) *Attorney, Agent, or Firm* — Bozicevic Field & Francis, LLP; Paula A. Borden

(57) ABSTRACT

Methods are provided for detecting a glycosylated target protein in a sample. Aspects of the methods include: (a) contacting a sample comprising a probe-labeled glycosylated target protein with: (i) a first conjugate comprising a first nucleic acid tag linked to a first capture agent that specifically binds the target protein; (ii) a second conjugate comprising a second nucleic acid tag linked to a second capture agent that specifically binds the probe; and (iii) a bridging nucleic acid that hybridizes to the first and second nucleic acid tags; under conditions sufficient to specifically bind the first and second capture agents to the probe-labeled target protein and to hybridize the bridging nucleic acid to the first and second nucleic acid tags to produce a nucleic (Continued)

acid complex; and (b) detecting the nucleic acid complex. Also provided are compositions and kits useful in practicing various embodiments of the subject methods.

7 Claims, 7 Drawing Sheets

(52) U.S. Cl.
CPC ..... *G01N 2400/02* (2013.01); *G01N 2440/38* (2013.01); *G01N 2458/10* (2013.01)

(56) References Cited

U.S. PATENT DOCUMENTS

| | | |
|---|---|---|
| 2009/0111094 A1 | 4/2009 | Storhoff et al. |
| 2010/0104556 A1 | 4/2010 | Blankenstein et al. |
| 2011/0189690 A1 | 8/2011 | Shibasaki et al. |

OTHER PUBLICATIONS

Chang et al. Metabolic Labeling of Sialic Acids in Living Animals with Alkynyl Sugars. Angew. Chem. Int. Ed. 48:4030-4033. (Year: 2010).*
Nong et al. Solid-phase proximity ligation assays for individual or parallel protein analyses with readout via real-time PCR or sequencing. Nature Protocols 8(6): 1234-1248. (Year: 2013).*
Xie et al. Targeted Imaging and Proteomic Analysis of Tumor-Associated Glycans in Living Animals. Angew. Chem. Int. Ed. 53: 14082-14086. (Year: 2014).*
Zhang, X. Applications of azide-based bioorthogonal click chemistry in glycobiology. Molecules, 2013, 18, 7145-7159. (Year: 2013).*
Murray, R. Glycoproteins: crucial molecules for health. GlycoScience & Nutrition, 2003, 4(7), 1-10. (Year: 2003).*

* cited by examiner

METHOD FOR DETECTING PROTEIN-SPECIFIC GLYCOSYLATION

CROSS-REFERENCE

This application is a national stage application under 35 U.S.C. § 371 of PCT/US2016/041185, filed Jul. 6, 2016, which claims the benefit of U.S. Provisional Patent Application No. 62/189,630, filed Jul. 7, 2015, which applications are incorporated herein by reference in their entirety.

STATEMENT REGARDING FEDERALLY SPONSORED RESEARCH

This invention was made with government support under Grant No. GM059907 awarded by the National Institutes of Health. The government has certain rights in the invention.

INTRODUCTION

The reversible attachment of N-acetylglucosamine (GlcNAc) to serine or threonine side chains of intracellular proteins is a post-translational modification (PTM) termed O-GlcNAc. The O-GlcNAc modification regulates diverse cellular activities. O-GlcNAc is installed by a single enzyme, O-GlcNAc transferase (OGT), and removed by O-GlcNAc-ase (OGA). This modification is widespread—more than 3000 O-GlcNAc sites have been discovered in eukaryotic proteomes—and mediates cellular activities by regulating protein trafficking, conformational change, and by antagonizing phosphorylation. Many human pathologies exhibit aberrant O-GlcNAcylation of specific proteins. For example, hyper-glycosylation leads to altered enzymatic activity of phosphofructokinase in aggressive breast cancers, glycogen synthase in diabetes, and CaMKII in cardiovascular disease. For example, hypo-glycosylation of the tau protein leads to an Alzheimer's disease-like state in a mouse model. O-GlcNAc also regulates pluripotency and reprogramming in stem cells through the modification of numerous transcription factors. Recently, the O-GlcNAcylation of master pluripotency regulator OCT4 increased cells' ability to maintain pluripotency. Due to its central role in regulating cellular behavior, it is thus valuable to profile O-GlcNAcylation at a proteomic level to elucidate function. As such, methods of detecting protein specific glycosylation are of interest.

SUMMARY

Methods are provided for detecting a glycosylated target protein in a sample. Aspects of the methods include: (a) contacting a sample comprising a probe-labeled glycosylated target protein with: (i) a first conjugate comprising a first nucleic acid tag linked to a first capture agent that specifically binds the target protein; (ii) a second conjugate comprising a second nucleic acid tag linked to a second capture agent that specifically binds the probe; and (iii) a bridging nucleic acid that hybridizes to the first and second nucleic acid tags; under conditions sufficient to specifically bind the first and second capture agents to the probe-labeled target protein and to hybridize the bridging nucleic acid to the first and second nucleic acid tags to produce a target protein-bound nucleic acid complex; and (b) detecting the target protein-bound nucleic acid complex. Also provided are compositions and kits useful in practicing various embodiments of the subject methods.

The present disclosure provides a method for detecting a glycosylated target protein in a sample, the method comprising: (a) contacting a sample comprising a probe-labeled glycosylated target protein with: (i) a first conjugate comprising a first nucleic acid tag linked to a first capture agent that specifically binds the target protein; (ii) a second conjugate comprising a second nucleic acid tag linked to a second capture agent that specifically binds the probe; and (iii) a bridging nucleic acid that hybridizes to the first and second nucleic acid tags; under conditions sufficient to specifically bind the first and second capture agents to the probe-labeled target protein and to hybridize the bridging nucleic acid to the first and second nucleic acid tags to produce a target protein-bound nucleic acid complex; and (b) detecting the target protein-bound nucleic acid complex. The present disclosure provides a method for detecting a glycosylated target protein in a sample, the method comprising: (a) contacting a sample comprising a probe-labeled glycosylated target protein with: (i) a first conjugate comprising a first nucleic acid tag linked to a first capture agent that specifically binds the target protein; (ii) a second conjugate comprising a second nucleic acid tag linked to a second capture agent that specifically binds the probe; and (iii) a bridging nucleic acid that hybridizes to the first and second nucleic acid tags; under conditions sufficient to specifically bind the first and second capture agents to the probe-labeled target protein and to hybridize the bridging nucleic acid to the first and second nucleic acid tags to produce a glycosylated target protein-bound nucleic acid complex; and (b) detecting the glycosylated target protein-bound nucleic acid complex. In some cases, the target protein-bound nucleic acid complex (e.g., the glycosylated target protein-bound nucleic acid complex) comprises an amplicon and the detecting comprises: amplifying the amplicon to generate an amplification product; and detecting the amplification product to provide for detection of the glycosylated target protein. In some cases, the bridging nucleic acid comprises a first region complementary to the first nucleic acid tag and a second region complementary to the second nucleic acid tag. In some cases, the method further comprises, prior to step (a), contacting a sample comprising a metabolically tagged glycosylated protein with a reactive probe to produce the probe-labeled glycosylated target protein. In some cases, the sample is obtained from a eukaryotic cell comprising the metabolically tagged glycosylated protein. In some cases, the method further comprises contacting the eukaryotic cell with a tagged sugar under conditions sufficient to produce the metabolically tagged glycosylated protein. In some cases, the metabolically tagged protein comprises a first chemoselective tag. In some cases, the first chemoselective tag is an azide. In some cases, the reactive probe comprises a second chemoselective tag selected from the group consisting of an alkyne, an azide, a phosphine, a thiol, a maleimide or iodoacetyl, an aldehyde, an alkoxyamine. In some cases, the second chemoselective tag is an alkyne. In some cases, the first capture agent and the second capture agent are independently selected from a nucleic acid, a protein, a peptide, or a small molecule. In some cases, the first capture agent is an antibody. In some cases, the second capture agent is an antibody. In some cases, the first capture agent and the second capture agents are antibodies. In some cases, the method further comprises determining the amount of total target protein in the sample. In some cases, determining the amount of total target protein is carried out using a proximity-based ligation assay comprising: (a) contacting the sample with: (i) a third conjugate comprising a third nucleic acid tag linked to a third capture agent that specifically binds a first epitope in the target protein; (ii) a fourth conjugate comprising a fourth nucleic acid tag linked to a fourth capture agent that specifically a second epitope in the target protein; and (iii) a bridging nucleic acid that hybridizes to the third and fourth nucleic acid tags; under conditions sufficient to specifically bind the third and fourth capture agents to the probe-labeled target protein and to hybridize the bridging nucleic acid to the third and fourth nucleic acid tags to produce a total target protein-bound nucleic acid complex; and (b) detecting the target protein-bound nucleic acid complex. In some cases, the method comprises comparing the level of glycosylated target protein to the level of total target protein.

The present disclosure provides a composition comprising: (a) a first conjugate comprising a first nucleic acid tag linked to a first capture agent that is capable of specifically binding a target protein; and (b) a second conjugate comprising a second nucleic acid tag linked to a second capture agent that is capable of specifically binding a probe. In some cases, the composition further comprises: (c) a bridging nucleic acid that is complementary to the first and second nucleic acid tags. In some cases, the first capture agent and the second capture agent are independently selected from a nucleic acid, a protein, a peptide, or a small molecule. In some cases, the first capture agent is an antibody. In some cases, the second capture agent is an antibody. In some cases, the first capture agent is an antibody and the second capture agent is an antibody. In some cases, the first capture agent is an anti-target protein antibody and the second capture agent is an anti-biotin antibody or an avidin moiety. In some cases, the composition further comprises a probe-labeled glycosylated target protein.

The present disclosure provides a kit comprising: a first conjugate comprising a first nucleic acid tag linked to a first capture agent that is capable of specifically binding a target protein; and a second conjugate comprising a second nucleic acid tag linked to a second capture agent that is capable of specifically binding a probe. In some cases, the kit further comprises a bridging nucleic acid that is complementary to the first and second nucleic acid tags. In some cases, the first capture agent is an antibody. In some cases, the second capture agent is an antibody. In some cases, the first capture agent is an antibody and the second capture agent is an antibody. In some cases, the first capture agent is an anti-target protein antibody and the second capture agent is an anti-biotin antibody or an avidin moiety.

DEFINITIONS

Figure 1:
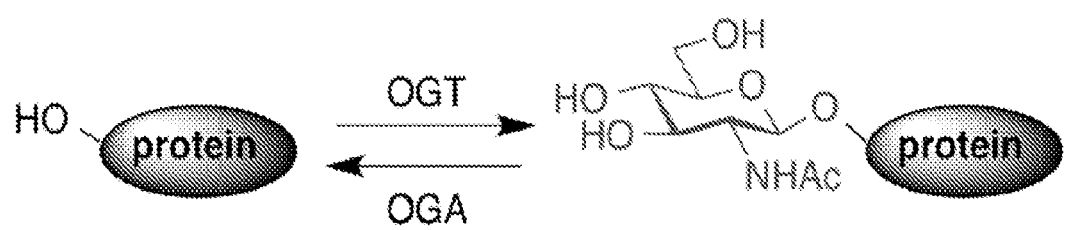
FIG. 1 depicts the reversible attachment of O-GlcNAc on Ser and Thr residues controlled by two conserved enzymes: O-GlcNAc transferase (OGT) and O-GlcNAc-ase (OGA).

Before describing exemplary embodiments in greater detail, the following definitions are set forth to illustrate and define the meaning and scope of the terms used in the description.

As used herein, the term "sample" relates to a material or mixture of materials, in some cases in liquid form, containing or suspected of containing one or more glycosylated proteins of interest. In some embodiments, the term refers to any plant, animal, fungal, or bacterial (or other microorganism) material containing cells, cellular metabolites, biomarkers, or other analytes of interest, such as, for example, tissue or fluid isolated from an individual (including without limitation plasma, serum, urine, cerebrospinal fluid, lymph, tears, saliva and tissue sections) or from in vitro cell culture constituents, as well as samples from the environment. A sample as described herein may or may not contain cells or cellular material. The term "sample" may also refer to a "biological sample". As used herein, the term "biological sample" refers to a whole organism or a subset of its tissues, cells or component parts (e.g., body fluids, including, but not limited to, blood, mucus, lymphatic fluid, synovial fluid, cerebrospinal fluid, saliva, amniotic fluid, amniotic cord blood, urine, vaginal fluid, semen, tears, serum, plasma, feces, swabs such as those obtained from the mouth, throat, nose, ears, wounds, or ulcers, tissue biopsies such as those obtained from tumors, organs or other body parts, or tissue sections such as those obtained from cadavers, skin, or hair).

A "biological sample" can also refer to a homogenate, lysate or extract prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term "cells" is used in its conventional sense to refer to the basic structural unit of living organisms, both eukaryotic and prokaryotic, having at least a cell membrane. In certain embodiments, cells include prokaryotic cells, such as from bacteria. In other embodiments, cells include eukaryotic cells, such as cells obtained from biological samples from animals, plants or fungi. Biological samples may include pathogens such as viruses. In some embodiments, the sample is a biological sample susceptible to infection by a pathogen, such as a virus.

As referred to herein, the term "eukaryotic cell" is used in its conventional sense to refer to one or more cells obtained from multi-cell organisms such animals, plants, fungi and yeast. As such, eukaryotic cells may include, but are not limited to, those obtained from yeast, fungi, plants, and animals including humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. In certain embodiments, eukaryotic cells include those obtained from a human being.

As used herein, the terms "determining," "measuring," "assessing," and "assaying" are used interchangeably and include both quantitative and qualitative determinations.

As used herein, the terms "affinity" and "avidity" have the same meaning and may be used interchangeably herein. "Affinity" refers to the strength of binding, increased binding affinity being correlated with a lower $K_D$.

Components of interest in a sample (e.g., glycosylated proteins of interest) are in some cases termed "sample analytes" herein. In some embodiments, the sample is a complex sample containing at least $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $10^9 10^{10}$, $10^{11}$, $10^{12}$ or more species of analyte. In certain embodiments, the sample is a sample containing 100 or fewer analytes, such as 50 or fewer, 20 or fewer, 10 or fewer, 5 or fewer, or even one analyte.

A "biopolymer" is a polymer of one or more types of repeating units, regardless of the source. Biopolymers may be found in biological systems and may include polypeptides, polynucleotides, sugars, carbohydrates, and analogs thereof.

As used herein, the term "polypeptide" refers to a polymeric form of amino acids of any length, including peptides that range from 2-50 amino acids in length and polypeptides that are greater than 50 amino acids in length. The terms "polypeptide" and "protein" are used interchangeably herein. The term "polypeptide" includes polymers of coded and non-coded amino acids, chemically or biochemically modified or derivatized amino acids, and polypeptides having modified peptide backbones in which the conventional backbone has been replaced with non-naturally occurring or synthetic backbones. A polypeptide may be of any convenient length, e.g., 2 or more amino acids, such as 4 or more amino acids, 10 or more amino acids, 20 or more amino acids, 50 or more amino acids, 100 or more amino acids, 300 or more amino acids, such as up to 500 or 1000 or more amino acids. "Peptides" may be 2 or more amino acids, such as 4 or more amino acids, 10 or more amino acids, 20 or more amino acids, such as up to 50 amino acids. In some embodiments, peptides are between 5 and 30 amino acids in length. The term "polypeptide" includes fusion proteins, including, but not limited to, fusion proteins with a heterologous amino acid sequence, fusions with heterologous native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. In some cases, a protein may be composed of two or more peptides and/or polypeptides.

As used herein the term "isolated," refers to a moiety of interest that is at least 60% free, at least 75% free, at least 90% free, at least 95% free, at least 98% free, and even at least 99% free from other components with which the moiety is associated with prior to purification.

The terms "nucleic acid," "nucleic acid molecule", "oligonucleotide" and "polynucleotide" are used interchangeably and refer to a polymeric form of nucleotides of any length, either deoxyribonucleotides or ribonucleotides, or compounds produced synthetically which can hybridize with naturally occurring nucleic acids in a sequence specific manner similar to that of two naturally occurring nucleic acids, e.g., can participate in Watson-Crick base pairing interactions. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, cDNA, recombinant polynucleotides, plasmids, vectors, isolated DNA of any sequence, control regions, isolated RNA of any sequence, nucleic acid probes, primers and any convenient synthetic nucleic acid sequence. The term "polynucleotide" is also meant to encompass nucleic acid analogs, and mixtures of analogs and naturally occurring nucleic acids. Any kind of nucleic acid, such as DNA and RNA, capable of sequence specific hybridization through formation of base pairs—or similar interactions between two moieties—may be utilized to implement the methods described herein, including artificial and unnatural nucleic acid analogs such as protein nucleic acid (PNA), locked nucleic acid (LNA), mannose nucleic acid (MNA), arabinonucleic acid (ANA), α-L-threofuranosyl-(3'→2') nucleic acid (TNA), cyclohexene nucleic acid (CeNA), 2'-fluoroarabinose nucleic acids (FNA), glycol nucleic acid (GNA), xeno nucleic acid (XNA), 2',3'-dideoxy-1',5'-anhydro-D-arabino-hexitol nucleic acid (HNA), intercalating nucleic acid (INA), bridged nucleic acid (BNA), and bicyclo-DNA. Sequence specific pairing of polynucleotides of interest that find use in the subject methods may involve natural Watson-Crick base pairing, Hoogsteen pairing, metal ion pairing, or other configurations or pairings between base moieties forming hydrogen bonds, metal ion interactions, or other types of moieties forming sequence specific pairing interactions such as unnatural base pairs (UBP) that may involve hydrogen bonds, hydrophobic interactions or other types of non-covalent bonds.

Specific pairing interactions of polynucleotides may involve natural, unnatural, artificial or modified bases. Analogs or moieties of interest include, but are not limited to, adenine, guanine, thymidine, cytosine, uridine, inosine, thiouridine, 5-bromouracil, methylated bases, 5-methylcytocine and 5-hydroxymethylcytocine, diaminopurine, diaminopyridine, isoguanine, isocytosine, 2'-deoxyinosine, 2-aminoadenine, xanthine, beta-d-glucopyranosyloxymethyluracil, d5SICS, dNaM, 2-amino-8-(2-thienyl)purine, pyridine-2-one, 7-(2-thienyl)imidazo[4,5-b]pyridine, pyrrole-2-carbaldehyde, 4-[3-(6-aminohexanamido)-1-propynyl]-2-nitropyrrole, 2,4-difluorotoluene, 4-methylbenzimidazole, isoquinoline, pyrrolo[2,3-b]pyridine, 2,6-bis(ethylthiomethyl)pyridine, pyridine-2,6-dicarboxamide, and mondentate pyridine.

Nucleic acid analogs of interest may include any convenient combination of backbones, bases (or analogs thereof), and pairing moieties that result in a molecule capable of sequence specific binding with a complementary nucleic acid analog of the same or different type which contains a complementary sequence in at least a portion of its sequence.

The term "sequence" may refer to a particular sequence of bases and/or may also refer to a polynucleotide having a particular sequence of bases. Thus a sequence may be information or may refer to a molecular entity, as indicated by the context of the usage.

The term "moiety" is used to refer to a portion of an entity or molecule, in some cases having a particular function, structure, or structural feature.

The terms "detectable moiety", "detectable tag" and "measureable moiety" are used interchangeably herein to refer to a tag, moiety, and/or molecule which has properties that can be detected and/or measured, directly or indirectly.

The terms "antibody," "immunoglobulin" and their plural referents include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins including an antigen-binding portion of an antibody and a non-antibody protein. The antibodies may be bound to an entity that enables their detection, e.g., a radioisotope, an enzyme which generates a detectable product, a fluorescent protein, and the like. The antibodies may be further covalently or non-covalently conjugated to other moieties, such as members of specific binding pairs, e.g., biotin (member of biotin-avidin/streptavidin specific binding pair), and the like. The antibodies may also be bound to a solid support, including, but not limited to, polystyrene plates or beads, and the like. Also encompassed by the terms are Fab', Fv, F(ab')2, and or other antibody fragments that retain specific binding to antigen. Antibodies may exist in a variety of other forms including, for example, Fv, Fab, and (Fab')2, as well as bi-functional (i.e. bi-specific) hybrid antibodies (e.g., Lanzavecchia et al., *Eur. J. Immunol.* 17, 105 (1987)) and in single chains (e.g., Huston et al., *Proc. Natl. Acad. Sci. USA*, 85, 5879-5883 (1988); Bird et al., *Science*, 242, 423-426 (1988); see Hood et al., *Immunology*, Benjamin, N.Y., 2nd ed. (1984), and Hunkapiller and Hood, *Nature*, 323, 15-16 (1986)).

The terms "capable of hybridizing," "hybridizing", and "hybridization" as used herein refers to binding between complementary or partially complementary molecules, for example as between the sense and anti-sense strands of double-stranded DNA. Such binding is commonly non-covalent binding, and is specific enough such that binding may be used to differentiate between highly complementary molecules and others less complementary. Examples of highly complementary molecules include complementary oligonucleotides, DNA, RNA, and the like, which include a region of nucleotides arranged in the nucleotide sequence that is exactly complementary to a second nucleic acid sequence; examples of less complementary oligonucleotides include ones with nucleotide sequences including one or more nucleotides not in the sequence exactly complementary to a second oligonucleotide.

The term "complementary" references a property of specific binding between pairs of specific binding moieties. Specific binding moieties are complementary if they specifically bind to each other. A pair of specific binding moieties that are each polynucleotides (including naturally occurring nucleic acids and nucleic acid analogs) may be complementary based on their sequence complementarity. In some cases, polynucleotides are complementary if they bind to each other in a hybridization assay under stringent conditions. Portions of polynucleotides are complementary to each other if they follow conventional base-pairing rules, e.g. A pairs with T (or U) and G pairs with C, or if they follow any convenient sequence specific pairing interactions such as unnatural base pairs (UBP) that may involve hydrogen bonds, hydrophobic interactions or other types of non-covalent bonds. "Complementary" includes embodiments in which there is an absolute sequence complementarity, and also embodiments in which there is a substantial sequence complementarity. Additional examples of specific binding pairs which may be considered complementary include antibody-antigen binding pairs, receptor-ligand binding pairs, nucleic acid aptamer-protein binding pairs and the like.

"Absolute sequence complementarity" means that there is 100% sequence complementarity between a first polynucleotide and a second polynucleotide, i.e. there are no insertions, deletions, or substitutions in either of the first and second polynucleotides with respect to the other polynucleotide (over the complementary region). Put another way, every base (or analog thereof) of the complementary region is paired with its complementary base (or analog thereof) by base-pairing or other specific pairing as described herein.

"Substantial sequence complementarity" permits one or more relatively small (in some cases, less than 10 bases, e.g. less than 5 bases, typically less than 3 bases, more typically a single base) insertions, deletions, or substitutions in the first and or second polynucleotide (over the complementary region) relative to the other polynucleotide. The complementary region is the region that is complementary between a first polynucleotide and a second polynucleotide (e.g. a distinct sequence of a nucleic acid target molecule and a nucleic acid capture agent). Complementary sequences are in some cases embedded within larger polynucleotides, thus two relatively long polynucleotides may be complementary over only a portion of their total length. The complementary region may be of any convenient length, and is in some cases at least 5 bases long, such as at least 7 bases long, at least 12 bases long, at least 15 bases long, at least 20 bases long, at least 25 bases long, at least 30 bases long, at least 40 bases long, at least 50 bases long, at least 60 bases long, at least 70 bases long, at least 80 bases long, at least 90 bases long, at least 100 bases long, at least 200 bases long, at least 300 bases long, at least 400 bases long, at least 500 bases long, at least 600 bases long, at least 700 bases long, at least 800 bases long, at least 1000 bases long, at least 2000 bases long, at least 3000 bases long, at least 4000 bases long, at least 5000 bases long, or even longer.

The terms "hybridizing specifically to," "specific hybridization," "selectively hybridize to," and the like are used herein to refer to the binding, duplexing, or hybridizing of a nucleic acid molecule preferentially to a particular nucleotide sequence under "stringent conditions."

The term "stringent conditions" refers to conditions under which a first molecule, e.g., a first nucleic acid, will bind preferentially to a second molecule, e.g., a second nucleic acid, and to a lesser extent to, or not at all to, e.g., other sequences. Put another way, the term "stringent hybridization conditions" as used herein refers to conditions that are compatible to produce complexes (e.g., duplexes) between complementary binding members, e.g., between a sequence of a nucleic acid capture agent and a complementary sequence of a target nucleic acid. In some instances, the first and second complementary binding members include molecules selected from a protein, such an antibody, which specifically binds to a complementary antigen and not to other molecules under stringent conditions. Stringent conditions for specific binding involving biomolecules such as proteins may include high salt concentrations and high temperatures.

"Stringent hybridization conditions" and "stringent hybridization wash conditions" in the context of nucleic acid hybridization are sequence dependent, and are different under different environmental parameters. Stringent hybridization conditions can include, e.g., hybridization in a buffer including 50% formamide, 5× saline sodium citrate (SSC), and 1% sodium dodecyl sulfate (SDS) at 42° C., or hybridization in a buffer including 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Yet additional stringent hybridization conditions include hybridization at 60° C. or higher and 3×SSC (450 mM NaCl/45 mM sodium citrate) or incubation at 42° C. in a solution containing 30% formamide, 1M NaCl, 0.5% sodium sarcosine, 50 mM 2-(N-morpholino)ethanesulfonic acid, pH 6.5. Those of ordinary skill will readily recognize that alternative but comparable hybridization and wash conditions can be utilized to provide conditions of similar stringency.

In certain embodiments, the stringency of the wash conditions may affect the degree to which nucleic acid molecules specifically hybridize. Suitable wash conditions may include, e.g.: a salt concentration of about 0.02 M at pH 7 and a temperature of at least about 50° C. or about 55° C. to about 60° C.; or, a salt concentration of about 0.15 M NaCl at 72° C. for about 15 min; or, a salt concentration of about 0.2×SSC at a temperature of at least about 50° C. or about 55° C. to about 60° C. for about 1 to about 20 min; or, multiple washes with a solution with a salt concentration of about 0.1×SSC containing 0.1% SDS at 20 to 50° C. for 1 to 15 min; or, equivalent conditions. Stringent conditions for washing can also be, e.g., 0.2×SSC/0.1% SDS at 42° C. In instances wherein the nucleic acid molecules are oligodeoxynucleotides (i.e. oligonucleotides made up of deoxyribonucleotide subunits), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, et al., *Molecular Cloning: A Laboratory Manual*, Second Edition, (1989) Cold Spring Harbor, N.Y.), for detailed descriptions of equivalent hybridization and wash conditions and for reagents and buffers, e.g., SSC buffers and equivalent reagents and conditions.

Stringent hybridization conditions may also include a "prehybridization" of aqueous phase nucleic acids with complexity-reducing nucleic acids to suppress repetitive sequences. For example, certain stringent hybridization conditions include, prior to any hybridization to surface-bound polynucleotides, hybridization with random sequence synthetic oligonucleotides (e.g. 25-mers), or the like. Other stringent hybridization conditions are known in the art and may also be employed, as appropriate.

The term "amplicon" as used herein refers to a nucleic acid complex that is the source of an amplified nucleic acid or the initiating nucleic acid in a nucleic acid amplification reaction. A "nucleic acid complex" refers to two or more joined nucleic acids including but not limited to e.g., a duplex, a triplex, a quadruplex, a pentaplex, a hexaplex, and the like. The nucleic acids of a nucleic acid complex may be joined, e.g., hybridized, through hydrogen bonding interactions including Watson-Crick base-pairing. In some instances, two or more nucleic acids of a nucleic acid complex may be ligated together through the covalent linking of two ends of individual nucleic acid molecules, e.g., through the use of an enzyme that catalyzes the covalent joining of nucleic acids or ligases. In an amplification reaction additional amplification product may be amplified from amplification product that is the result of the initial amplicon and, as such, the term amplicon may also refer to the product of an amplification reaction which is subsequently used in further amplification, however, as used herein, an amplicon generally refers to the initial polynucleotide or polynucleotide complex from which amplification is initiated.

The term "ligase" as referred to herein refers collectively to enzymes that catalyze the covalent joining of two adjacent ends of a nucleic acid molecule or molecules. For example, a nucleic acid ligase may catalyze the formation of a phosphodiester bond between juxtaposed 5' phosphate and 3' hydroxyl termini in single stranded or double stranded nucleic acid, including, e.g., ssDNA, dsDNA, ssRNA, and dsRNA. Ligases may ligate nucleic acid hybridized to a complementary nucleic acid or may ligate in the absence of a complementary nucleic acid. Any convenient ligase may find use in the methods described herein including but not limited to, e.g., naturally occurring ligases, synthetic or recombinant ligases, mutant ligases, DNA ligases, RNA ligases, sticky-end ligases, blunt end ligases, nick-repair ligases, thermostable ligases, thermolabile ligases, T4 DNA ligase, T3 DNA ligase, T7 DNA ligase, *E. coli* DNA ligase, Taq DNA ligase, *Thermococcus* DNA ligase, *Chlorella* virus DNA Ligase, T4 RNA ligase 1, T4 RNA ligase 2, *Methanobacterium thermoautotrophicum* DNA/RNA ligase, and the like.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal concentration, and salt concentration. Primers are generally of a length compatible with their use in synthesis of primer extension products, and may be in the range of between 8 to 100 nucleotides in length, such as 10 to 75, 15 to 60, 15 to 40, 18 to 30, 20 to 40, 21 to 50, 22 to 45, 25 to 40, and so on, including in the range of between 18-40, 20-35, 21-30 nucleotides long, and any length between the stated ranges. In some instances, primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

The terms "bind" and "bound" as used herein refer to a binding interaction between two or more entities. Where two entities, e.g., molecules, are bound to each other, they may be directly bound, i.e., bound directly to one another, or they may be indirectly bound, i.e., bound through the use of an intermediate linking moiety or entity. In either case the binding may be covalent; e.g., through covalent bonds; or non-covalent, e.g., through ionic bonds, hydrogen bonds, electrostatic interactions, hydrophobic interactions, Van der Waals forces, or a combination thereof.

As used herein, the terms "chemoselective functional group" and "chemoselective tag" are used interchangeably and refer to chemoselective reactive groups that selectively react with one another to form a covalent bond. Chemoselective functional groups of interest include, but are not limited to, thiols and maleimide or iodoacetamide, as well as groups that can react with one another via Click chemistry, e.g., azide and alkyne groups (e.g., cyclooctyne groups).

The term "contacting" is used herein in its conventional sense to refer to placing two or more aspects in proximity or providing an interaction or communication between two or more aspects. For example, contacting may mean exposing (e.g., incubating with and/or allowing direct physical contact between) one aspect (e.g., an isotopic labeling composition) to another aspect (a cell). Contacting may also mean, for example, allowing one aspect to integrate with and/or penetrate and/or chemically react with another aspect.

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step may be performed after an incubation or waiting time after completion of the previous step, e.g., a few minutes to an overnight waiting time.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a target protein" includes a plurality of such target proteins and reference to "the target protein" includes reference to one or more target proteins and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

As summarized above, aspects of the present disclosure include a method for detecting a glycosylated target protein in a sample. Aspects of the method include labelling a metabolically tagged glycosylated target protein with a reactive probe to produce a probe-labeled glycosylated target protein. Detection of the probe-labeled glycosylated target protein may be achieved by specifically binding two conjugates to the probe-labeled glycosylated protein: a first conjugate which specifically binds the target protein and a second conjugate which specifically binds the probe. The first and second conjugates include first and second nucleic acid tags, respectively. When the first and second conjugates are specifically bound to the probe-labeled glycosylated target protein, the first and second nucleic acid tags are in proximity to each other. Any convenient methods of proximity ligation assays may be adapted in the subject methods to provide for detection of the specifically bound probe-labeled glycosylated target protein.

Aspects of the method include hybridizing a bridging nucleic acid to the proximate first and second nucleic acid tags to produce a target protein-bound nucleic acid complex that may be subsequently detected using polymerase chain reaction (PCR). The bridging nucleic acid includes a first region complementary to the first nucleic acid tag and a second region complementary to the second nucleic acid tag. The first conjugate includes a first capture agent that specifically binds to target protein (e.g., glycosylated or non-glycosylated target protein). The second conjugate includes a second capture agent that specifically binds the probe which may installed on the target protein via chemoselective labelling to a tagged sugar on a metabolically tagged protein (e.g., target protein or non-target protein). As such, in some cases, the formation of the target protein-bound nucleic acid complex may occur only for target proteins that are metabolically tagged glycosylated target proteins. Non-target proteins and target proteins that are not metabolically tagged may be easily distinguished from the glycosylated target protein using the subject methods.

Figure 3:
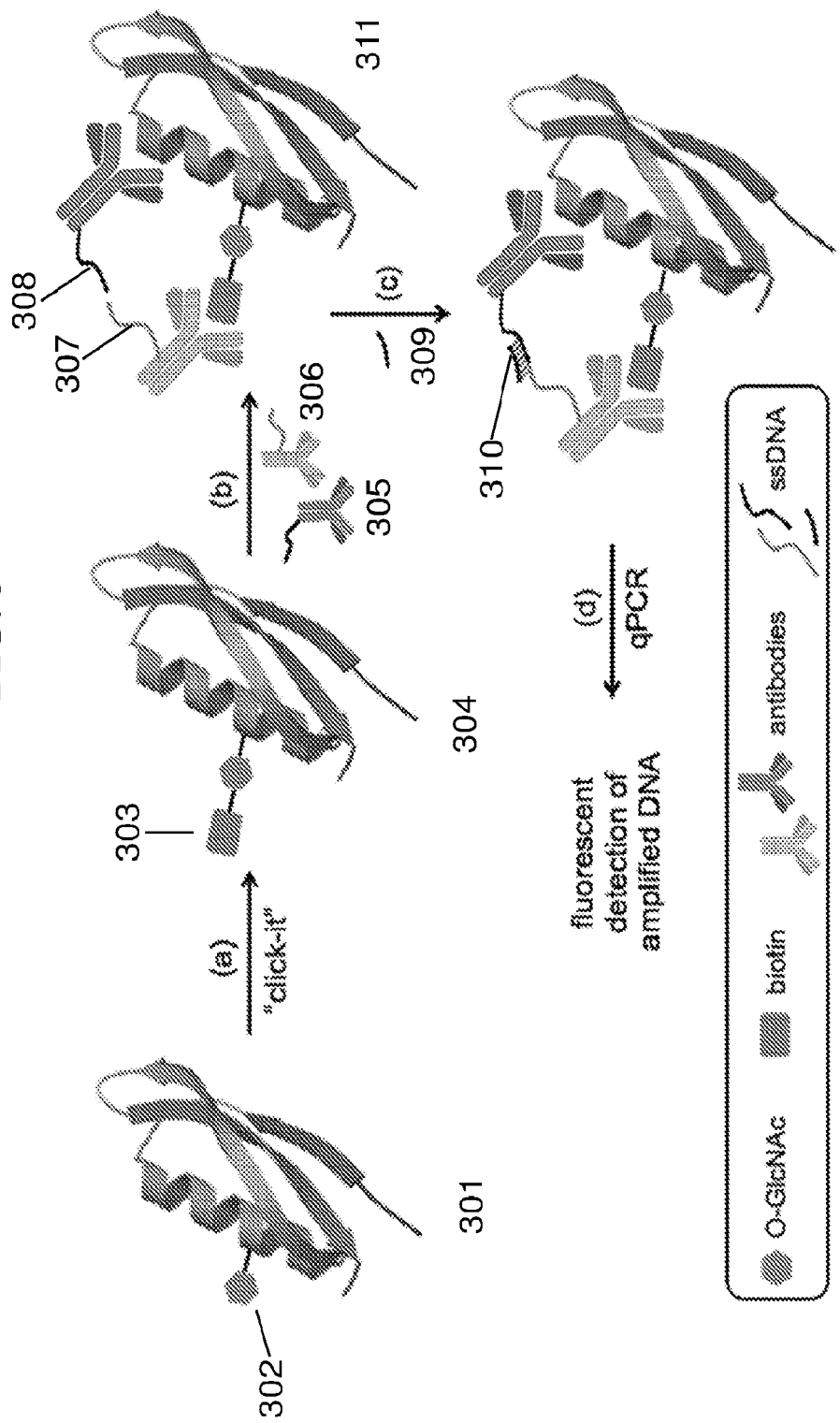
FIG. 3 shows a scheme depicting an exemplary workflow of the subject methods (in some cases, termed Glyco-Seq): (a) Biotin is appended onto O-GlcNAc using the "Click-it" method; (b) Proteins are incubated with antibody-DNA conjugates targeted to both biotin and the protein of interest; (c) Treatment with a short strand of DNA that is complementary to both single-stranded DNAs, and subsequent ligation allows for (d) detection of the resultant duplex DNA by standard qPCR methods.

FIG. 3 shows a scheme depicting an exemplary workflow of the subject methods (Glyco-Seq). In step (a), biotin (303) is attached onto a metabolically labelled O-GlcNAc (302) of target protein (301) using the "Click-it" method. In step (b), the biotin probe-labelled target protein (304) is incubated with first and second antibody-DNA conjugates targeted to either biotin (306) or the target protein (305). Step (c) depicts the treatment of the specifically bound target protein 311 with a bridging nucleic acid (309), i.e., a short strand of DNA that is complementary to both single-stranded nucleic acid tags (307 and 308) of the first and second conjugates to produce a target protein-bound nucleic acid complex (310). In step (d), detection of the resultant complex is achieved by conventional qPCR methods.

Each of these components that find use in the subject methods and compositions are now described in more detail, followed by further details of the methods of using the same.

Probe-Labeled Glycosylated Target Protein

Any convenient samples (e.g., as defined herein) may be analyzed according to the subject methods. The sample may include, or be suspected of including, one or more glycosylated target proteins of interest. The compositions and methods of the present disclosure may be utilized in connection with the qualitative and/or quantitative detection of any of a wide variety of glycosylated target proteins of interest. As used herein, the term "a target protein" refers to all members of the target protein family, and fragments thereof. The target protein may be any protein of interest, such as a therapeutic or diagnostic target, including but not limited to: hormones, growth factors, receptors, enzymes, cytokines, osteoinductive factors, colony stimulating factors and immunoglobulins. The term "target protein" is intended to include recombinant and synthetic molecules, which can be prepared using any convenient recombinant expression methods or using any convenient synthetic methods, or purchased commercially. A target protein may be isolated, substantially purified, or present within the native milieu (e.g., on a cell surface or within a cell, including within a host animal, e.g., a mammalian animal, such as a murine host (e.g., rat, mouse), hamster, canine, feline, bovine, swine, and the like). Protein targets of interest include, for example, cell surface receptors, signal transduction factors, and hormones. Nucleic acid targets of interest include, for example, DNA and RNA targets. Cellular targets of interest include, for example, mammalian cells (particularly human cells, e.g., human cancer cells) stem cells, and bacterial cells.

In some embodiments, the glycosylated target protein is present in vitro in a cell-free reaction. In other embodiments, the glycosylated target protein is present in a cell and/or displayed on the surface of a cell. In many embodiments of interest, the glycosylated target protein is in a living cell; on the surface of a living cell; in a living organism, e.g., in a living multicellular organism. Suitable living cells include cells that are part of a living multicellular organism; cells isolated from a multicellular organism; immortalized cell lines; and the like. The protein may be composed of D-amino acids, L-amino acids, or both, and may be further modified, either naturally, synthetically, or recombinantly, to include other moieties. For example, the glycosylated target polypeptide may be a lipoprotein, a glycoprotein, or other such modified protein.

In some embodiments, the subject method includes contacting a eukaryotic cell with a tagged sugar under conditions sufficient to produce a metabolically tagged glycosylated protein. Aspects of the method include metabolically embedding a chemoselective tag into one or more molecules (e.g., glycans). By "metabolically embedding", as used herein, is meant inserting an aspect (e.g., one or more chemoselective tags) into one or more metabolic processes (e.g., metabolic processes occurring within a eukaryotic cell). In some aspects, metabolic processes are associated with a glycan biosynthetic pathway (e.g., the gna1Δ yeast hexosamine biosynthetic pathway). As used herein, the term "glycan" refers to a polysaccharide or oligosaccharide.

In some cases, the target protein is tagged with an azido-sugar. Molecules comprising an azide and suitable for use in the present invention, as well as methods for producing azide-comprising molecules suitable for use in the present disclosure, are well known in the art. Any convenient methods of metabolically tagging a glycosylated target protein may be adapted for use in the subject methods. In general, the target protein includes at least one azide for reaction with the second conjugate according to the subject methods, but may comprise 2 or more, 3 or more, 5 or more, 10 or more azides. The number of azides that may be present in a target protein may vary according to the particular application of the reaction, the nature of the target protein itself, and other considerations which will be readily apparent to the ordinarily skilled artisan in practicing the invention as disclosed herein.

The target protein can be generated in vitro and then introduced into the cell using any of a variety of methods well known in the art (e.g., microinjection, liposome or lipofectin-mediated delivery, electroporation, etc.), which methods will vary according to the nature of the protein to be targeted for detection and can be readily and appropriately selected by the ordinarily skilled artisan. The final target protein can also be generated in vivo by exploiting a host cell's natural biosynthetic machinery. For example, the cell can be provided with a biocompatible azide-derivative of a substrate for synthesis of the desired target protein, which substrate is processed by the cell to provide an azide-derivative of the desired final target protein. For example, where the target protein is a cell surface glycoprotein, the cell can be provided with an azide derivative of a sugar residue found within the glycoprotein, which is subsequently processed by the cell through natural biosynthetic processes to produce a modified glycoprotein having at least one modified sugar moiety comprising an accessible azide group.

The metabolically tagged target protein can also be produced in vivo using any convenient methods. For example, unnatural amino acids having azides can be incorporated into recombinant polypeptides expressed in E. coli (see, e.g., Kiick et al. (2000) Tetrahedron 56:9487). Such recombinantly produced polypeptides can be detected in a sample according to the subject methods.

In one embodiment, the target molecule is a carbohydrate-containing molecule (e.g., a glycoprotein; a polysaccharide; etc.), and an azide group is introduced into the target molecule using a synthetic substrate. In some embodiments, the synthetic substrate is an azide derivative of a sugar utilized in production of a glycosylated molecule. In some embodiments, the synthetic substrate is an azide derivative of a sugar utilized in production of a cell surface molecule, e.g., in the glycoprotein biosynthetic pathway. For example, the host cell can be provided with a synthetic sialic acid azido-derivative, which is incorporated into the pathway for sialic acid biosynthesis, eventually resulting in the incorporation of the synthetic sugar residue in glycoproteins. In some embodiments, the glycoproteins are displayed on the cell surface.

In one example, the synthetic substrate is an azido derivative of mannosamine of the general formula:

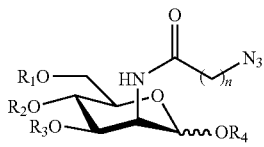

where n is from 1 to 6, generally from 1 to 4, more usually 1 to 2, and $R_1$, $R_2$, $R_3$, and $R_4$ are independently hydrogen or acetyl. In some embodiments, the substrate is N-azidoacetylmannosamine (n=1) or an acetylated derivative thereof, or N-azidopropanoylmannosamine (n=2) or an acetylated form thereof.

In another embodiment, the synthetic substrate is an azido sugar derivative of a general formula of, for example:

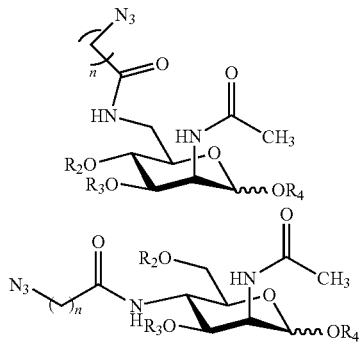

either of which can be incorporated into the sialic acid biosynthesis pathway, and where n is from 1 to 6, generally from 1 to 4, more usually 1 to 2, and $R_2$, $R_3$, and $R_4$ are independently hydrogen or acetyl.

In another embodiment, the synthetic substrate is an azido sugar derivative of a general formula of, for example:

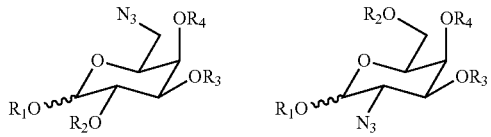

where $R_1$, $R_2$, $R_3$, and $R_4$ are independently hydrogen or acetyl, and where the synthetic substrate is incorporated into biosynthetic pathways involving fucose.

In another embodiment, the synthetic substrate is an azido sugar derivative of a general formula of, for example:

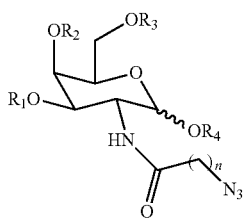

where n is from 1 to 6, generally from 1 to 4, more usually 1 to 2, and $R_1$, $R_2$, $R_3$, and $R_4$ are independently hydrogen or acetyl, and which is incorporated into biosynthetic pathways involving galactose.

As such, a variety of methods may be used to provide metabolically tagged glycosylated proteins, e.g., in a sample of interest. In some cases, the metabolically tagged glycosylated proteins include a metabolic tag that is an azide.

Any convenient methods and functional groups that find use in bioorthogonal or chemoselective conjugation reactions may be adapted for use in the subject methods to label a metabolically tagged glycosylated protein with a probe, e.g., via chemoselective reaction with the metabolic tag. Chemoselective functional groups of interest which may find use in the subject methods as either metabolic tags or in reactive probes which are capable of conjugation to the metabolic tags, include but are not limited to, aldehydes, azides, nitrones, nitrile oxides, diazo compounds, tetrazines, tetrazoles, quadrocyclanes, alkenes, alkynes (e.g., strained alkynes) and iodobenzenes. Bioorthogonal ligation reactions of interest include, but are not limited to, those reactions described in Table 1 of Debets et al. "Bioorthogonal labelling of biomolecules: new functional handles and ligation methods", Org. Biomol. Chem., 2013, 11, 6439-6455, the disclosure of which is herein incorporated by reference. In certain embodiments, the metabolically tagged protein includes an azide tag and may be labelled with an azide-reactive probe. Any convenient azide-reactive functional groups may be utilized to provide for chemoselective ligation of a reactive probe to a metabolically tagged protein that includes an azide tag.

Figure 2:
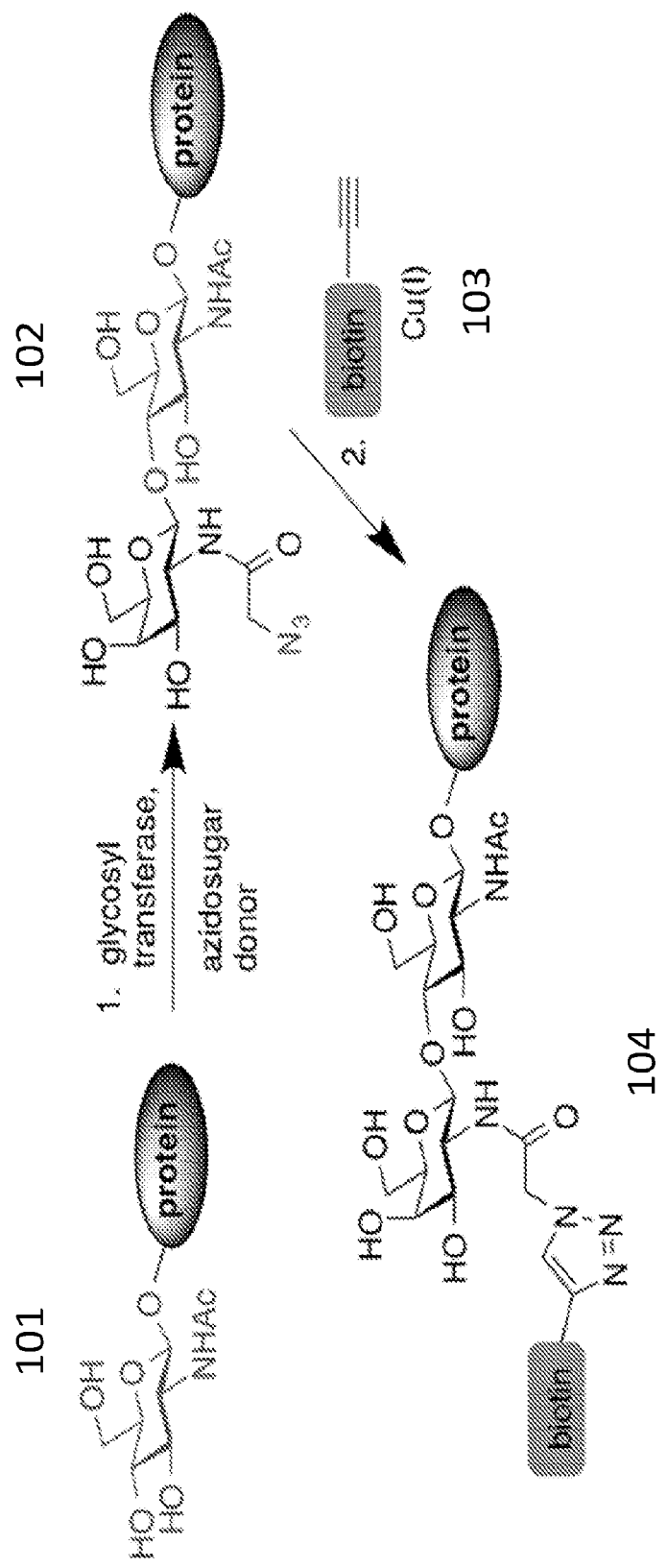
FIG. 2 shows a scheme depicting the "Click-it" method for appending biotin onto O-GlcNAc.

The "Click-it" method of detecting O-GlcNAc in lysates may be adapted for use in the subject methods to attach any convenient probe (e.g., as described herein) to a metabolically azide tagged and glycosylated target protein. In some cases, a probe such as a biotin moiety may be attached onto O-GlcNAc for facile detection (FIG. 2). FIG. 2 depicts an exemplary scheme for metabolically tagging a glycosylated target protein with a tagged sugar and then subsequently labelling it via a chemoselective conjugation (e.g., Click-it conjugation). First, O-GlcNAc is chemo-enzymatically modified by treatment with a permissive galactose transferase that introduces an azide-containing monosaccharide (N-azidoacetylgalactosamine, GalNAz). The azide is then reacted with an alkyne-biotin reagent and detection using anti-biotin antibodies is then performed. All O-GlcNAcylated proteins in a sample (e.g., a cell lysate) are simultaneously labelled (e.g., biotinylated) using the method. The detection of the O-GlcNAcylation state of a particular target protein may then be achieved via a second binding event of the target protein for subsequent analysis.

In some embodiments, the present disclosure provides for attachment of a reactive probe to an azide-modified target protein. The methods generally involve reacting an azide-modified target protein with a reactive probe including a strained alkyne (e.g., a cycloalkyne) to chemoselectively label the target protein with the probe.

Strained Alkynes

Any convenient strained alkynes may find use in the subject methods to label a glycosylated target protein of interest with a probe. As used herein, the term "strained alkyne" refers to an alkyne containing group or molecule where the alkyne has increased reactivity due to an inherent steric strain (e.g., a ring strain) on the linear alkyne group. An alkyne of interest may be strained in a variety of ways, such as the introduction of a ring structure, or the introduction of steric repulsion into the alkyne containing group to place mechanical stress on the carbon-carbon triple bond which can increase its reactivity. Strained alkynes of interest include those that find use in strain-promoted azide alkyne cycloaddition reactions (SPAAC), including azide bioconjugation reactions. In some cases, the "strained alkyne" is a cyclic alkyne, such as a cycloheptyne, a cyclooctyne, a cyclononyne, or a heterocyclic analog thereof.

A variety of strained alkynes may be adapted for incorporation into a reactive strained alkyne-labeled probe for use in labelling the glycosylated target protein. As used herein, the term "reactive probe" refers to a reagent for labelling a metabolically tagged and glycosylated target protein that includes a probe moiety and a chemoselective functional group compatible with the metabolic tag of interest. In some cases, the reactive probe is a "reactive strained alkyne-labeled probe" that includes a strained alkyne (e.g., as described herein) that is modified to include a linked probe (e.g., as described herein). Any of the strained alkynes described herein may be adapted to include an optional linker for attachment to a probe of interest, e.g., via covalent attachment of a linker or cargo agent to a hydroxyl group or a carboxylic acid group, or derivative thereof, of the strained alkynes described herein.

In certain embodiments, the strained alkyne is described by the formula:

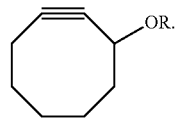

OCT 1: R = CH$_2$PhCO$_2$H
OCT 2: R = CH$_2$CO$_2$H

In certain embodiments, the strained alkyne is described by the formula:

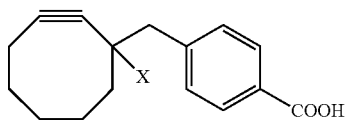

OCT 3: R = H
MOFO: R = F where X in some cases may be H or F.

In certain embodiments, the strained alkyne is described by the formula:

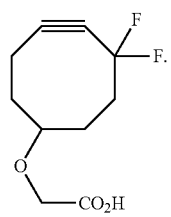 [SMILES: O=C(O)COC1CCC#CC(F)(F)CC1]

In certain embodiments, the strained alkyne is described by the formula:

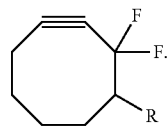

DIFO 2: R = CH$_2$PhCO$_2$H
DIFO 3: R = CH$_2$CO$_2$H

In certain embodiments, the strained alkyne is described by the formula:

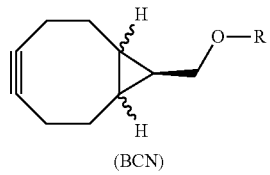

(BCN)

where R is H or an optional linker.

In certain embodiments, the strained alkyne is described by the formula:

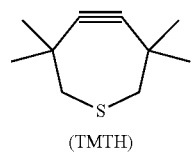

(TMTH)

where an optional linker or cargo agent may be attached at any convenient location of the TMTH strained alkyne, such as at a ring position alpha to the S atom.

In certain embodiments, the strained alkyne is described by the formula:

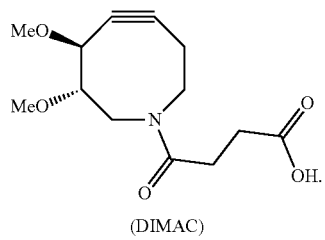 [SMILES: CO[C@H]1C#CCCN(C(=O)CCC(=O)O)C[C@@H]1OC]

(DIMAC)

In certain embodiments, the strained alkyne is described by the formula:

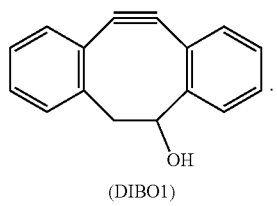

(DIBO1)

In certain embodiments, the strained alkyne is described by the formula:

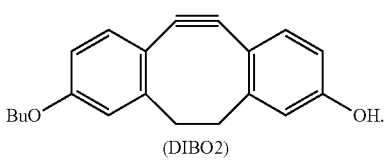
(DIBO2)

In certain embodiments, the strained alkyne is described by the formula:

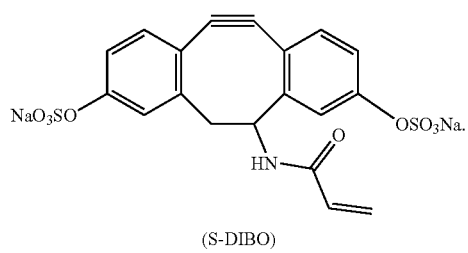
(S-DIBO)

In certain embodiments, the strained alkyne is described by the formula:

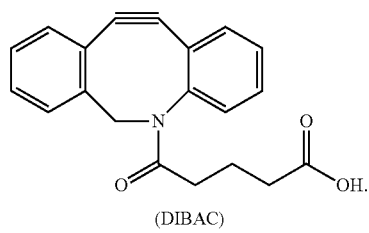 [SMILES: O=C(O)CCCC(=O)N1Cc2ccccc2C#Cc2ccccc21]
(DIBAC)

In certain embodiments, the strained alkyne is described by the formula:

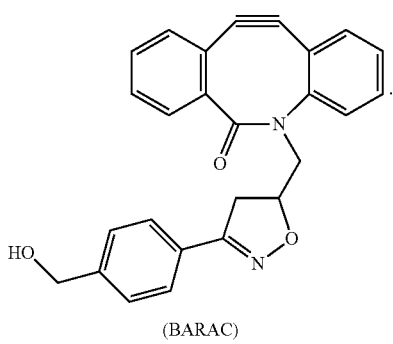 [SMILES: O=C1c2ccccc2C#Cc2ccccc2N1CC1CC(c2ccc(CO)cc2)=NO1]
(BARAC)

In certain embodiments, the strained alkyne is described by the formula:

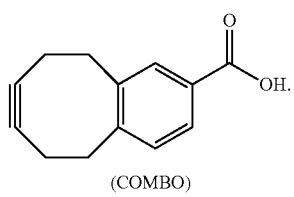
(COMBO)

Cyclooctynes of interest include, but are not limited to, dibenzoazocyclooctyne (DBCO/DIBAC), a dibenzocyclooctyne (DIBO) (e.g., DIBO1, DIBO2 or S-DIBO), a difluorocyclooctyne (DIFO) (e.g., DIFO1, 2 or 3), OCT1, OCT2, OCT3, MOFO, BCN, TMTH, DIMAC, BARAC, COMBO, and fluorogenic cyclooctynes such as CoumBARAC or Fl-DIBO. In certain emodiments, the cyclooctyne is selected from: dibenzoazocyclooctyne, a dibenzocyclooctyne, a difluorocyclooctyne, OCT1, OCT2, OCT3, MOFO, BCN, TMTH, DIMAC, BARAC and COMBO.

In some embodiments, the cyclooctyne is selected from:

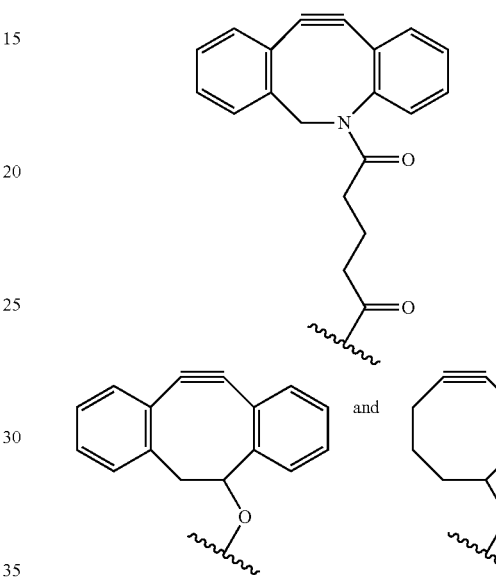

The strained alkyne may be covalently attached to a probe of interest directly or indirectly via an optional linker (L) (e.g., as described herein). Exemplary linking groups and linkages and methods of using the same are described in e.g., Hermanson, "Bioconjugate Techniques" 2nd Edition, Academic Press, 2008. The linker may be cleavable or non-cleavable. For instance, in certain embodiments, L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, the linker (L) includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments, L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

Probes

Aspects of the subject methods include labelling a glycosylated target protein with a reactive probe. As used herein the term "probe" refers to a moiety that is capable of being recognized either directly or indirectly through a specific binding member. A reactive probe further includes (in addition to the probe moiety) a chemoselective group for conjugation to the metabolic label of interest. As such, a target protein to which a reactive probe has been chemoselectively attached (e.g., as described herein) may be specifically recognized via the binding of a compatible specific binding member which specifically binds to the probe (e.g., a capture agent).

In some cases, the probe is one member of a pair of specific binding moieties. Any convenient specific binding member may be utilized as a probe in the subject methods to label a target protein. In some embodiments, the probe comprises a nucleic acid segment, nucleic acid analog segment, protein (including, for instance, an antibody, receptor protein, or enzyme), ligand, receptor, substrate, or hapten.

The terms "specific binding," "specifically bind," and the like, refer to the ability of a first binding molecule or moiety (e.g., a target-specific binding moiety such as a capture agent or a first specific binding moiety) to preferentially bind directly to a second binding molecule or moiety (e.g., a target molecule or a second specific binding moiety) relative to other molecules or moieties in a reaction mixture. In certain embodiments, the affinity between a first binding molecule or moiety and a second binding molecule or moiety when they are specifically bound to each other is characterized by a $K_D$ (dissociation constant) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. In some cases, the affinity between a capture agent and analyte when they are specifically bound in a capture agent/analyte complex is at least $10^{-8}$ M, at least $10^{-9}$ M, or at least $10^{-10}$ M. In some instances, a specific binding interaction will discriminate between desirable and undesirable analytes in a sample with a specificity of 10-fold or more for a desirable analyte over an undesirable analytes, such as 100-fold or more, or 1000-fold or more.

As used herein, a "member of a specific binding pair" is a member of a pair of molecules or entities that takes part in a specific binding interaction. Where a first member of the specific binding pair is identified, the identity of the second member of the specific binding pair may be readily identifiable. It should be noted that when either member of the binding pair is referred to as the first member, the remaining member is understood to be the second member and vice versa. Examples of specific binding pair interactions include immune interactions such as antigen/antibody and hapten/antibody as well as non-immune interactions such as complementary nucleic acid binding, complementary protein-protein interactions, a sugar and a lectin specific therefore, an enzyme and an inhibitor therefore, an apoenzyme and cofactor, a hormone and a receptor therefore, biotin/avidin and biotin/streptavidin.

As used herein, the term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin affinity agent may also include a linker, e.g., -LC-biotin, -LC-LC-Biotin, -SLC-Biotin or -PEG$_n$-Biotin where n is 3-12.

Capture Agents

Aspects of the subject methods include contacting the sample with: a first conjugate including a first nucleic acid tag linked to a first capture agent that specifically binds a target protein; and a second conjugate including a second nucleic acid tag linked to a second capture agent that specifically binds a probe, to form a complex.

As used herein the terms "affinity agent" and "capture agent" are used interchangeably and refer to an agent that binds a target moiety (e.g., protein or probe) through an interaction that is sufficient to permit the agent to extract the target moiety of interest from a mixture of different analytes and/or other sample components. The binding interaction may be mediated by an affinity region of the capture agent. Capture agents may "specifically bind" to one or more target moieties. Thus, the term "capture agent" refers to a molecule or a multi-molecular complex which can specifically bind a target moiety, e.g., specifically bind a target protein or probe for the capture agent with a dissociation constant ($K_D$) of $10^{-6}$ or less without binding to other target moieties, such as $10^{-6}$ M or less, $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, $10^{-16}$ M or less, $10^{-17}$ M or less, $10^{-18}$ M or less, or even less.

The term "capture agent/target complex" refers to a complex that results from the specific binding of a capture agent with a target moiety (e.g., a target protein or a probe). The complex may be part of a larger complex (e.g., a sandwich complex). A capture agent and a target moiety for the capture agent will typically specifically bind to each other under "conditions suitable for specific binding", where such conditions are those conditions (in terms of salt concentration, pH, detergent, protein concentration, temperature, etc.) which allow for binding to occur between capture agents and analytes in solution. Such conditions, for example with respect to antibodies and their antigens, are well known in the art (see, e.g., Harlow and Lane (Antibodies: A Laboratory Manual Cold Spring Harbor Laboratory, Cold Spring Harbor, N.Y. (1989)). Conditions suitable for specific binding in some cases permit capture agents and target pairs that have a dissociation constant ($K_D$) of less than about $10^{-6}$ to bind to each other, but not with other capture agents or targets.

The first and second capture agents may be moieties that are capable of specifically binding to a target protein or probe of interest, respectively, when both brought into contact with the sample under suitable reaction conditions. The binding interaction is, in some cases, mediated by an affinity region of the capture agent and a complementary affinity region of the target protein or probe. Any convenient capture agents may be selected as first and second capture agents and utilized to specifically bind a target analyte or a probe into a complex. Aspects of the subject methods include producing a complex of a probe-labelled glycosylated target protein that is specifically bound to both the first and second capture agents.

In some cases, the capture agent is itself part of a larger complex that includes additional components which do not specifically interact with the target protein. In some cases, one or more components (e.g., as described herein) of the complex are contacted with the sample and specifically bind to the first or second capture agent.

Capture agents of interest include, but are not limited to, proteins such as antibodies, scaffolded protein ligands or proteins involved in known biomolecule interactions (e.g., polynucleotide binding proteins, protein-protein interactions, or avidin-biotin interactions), polynucleotides such as aptamers or polynucleotides with complementary sequences, peptides, enzyme substrates, antigens, haptens, small molecules, inhibitors, or an analog thereof. In some embodiments, the first capture agent and the second capture agent are independently selected from a nucleic acid (e.g., an aptamer or complementary polynucleotide sequence), a polypeptide (e.g., an antibody), and a small molecule (e.g., a hapten). In some cases, the first capture agent and the second capture agent are independently selected from a nucleic acid, a protein, a peptide, or a small molecule (e.g., an antibody, a hapten, an aptamer, etc).

Target-specific capture agents may have a variety of structures provided that they are capable of specifically binding to a target protein or probe of interest under suitable reaction conditions. For example, where the target molecule is a nucleic acid, a suitable target-specific capture agent may be a nucleic acid molecule having a region of sequence complementarity to a region of the target nucleic acid molecule, e.g., a region of substantial or absolute sequence complementarity. Where the target is a protein or fragment thereof a suitable target-specific capture agent may be an antibody capable of specifically binding to the target molecule. For example, where the target moiety is a probe such as a biotin moiety, a suitable target-specific capture agent may be an anti-biotin antibody or may be an avidin moiety (i.e., member of a pair of specific binding moieties that specifically binds a biotin moiety and is the protein family that includes avidin), such as avidin, streptavidin or neutravidin protein, or a derivative thereof. In certain embodiments, the first capture agent is an anti-target protein antibody and the second capture agent is an avidin moiety.

Additional binding members capable of specific interactions are known in the art and accordingly a suitable target-specific capture agent may be readily identified and prepared for a specific target molecule or analyte of interest using standard techniques.

Nucleic Acid Tags

Aspects of the present disclosure include specifically binding to a glycosylated target protein first and second conjugates comprising first and second nucleic acid tags, respectively. As used herein, the term "nucleic acid tag" refers to a polynucleotide that has a particular sequence which may be used to identify the analyte to which it is connected or bound. The first and second nucleic acid tags are selected such that they are together capable of hybridizing to a particular bridging nucleic acid to produce an amplicon (e.g., as described herein). In some cases, the set of nucleic acids including the first and second nucleic acid tags and the bridging nucleic acid together are capable or forming a nucleic acid complex that defines a unique amplicon which finds use in the subject methods to detect and/or quantitate the glycosylated target protein of interest.

Any convenient sequences of nucleic acids may be selected for use in the subject first and second nucleic acid tags to provide for detection of the target glycosylated target protein. The nucleic acid tags may be of any convenient length. In some instances, the nucleic acid tag is at least 6 nucleotides in length, including but not limited to e.g., at least 10 nucleotides in length, at least 15 nucleotides in length, at least 16 nucleotides in length, at least 17 nucleotides in length, at least 18 nucleotides in length, at least 19 nucleotides in length, at least 20 nucleotides in length, at least 25 nucleotides in length, at least 30 nucleotides in length, and may be as long as 60 nucleotides in length or longer, where the length of the nucleic acid tags will generally range from 10 to 50 nucleotides in length, including but not limited to, e.g., from about 15 to 50 nucleotides in length, or from about 20 to 35 nucleotides in length.

As used herein, the term "bridging nucleic acid" refers to any polynucleotide that joins two or more separate polynucleotides or two termini of a single polynucleotide by simultaneously hybridizing with complementary regions on each polynucleotide or complementary regions of the polynucleotide termini. In certain instances, a bridging polynucleotide joins two target protein-bound nucleic acid tags by simultaneously hybridizing with a first complementary region of a first nucleic acid tag and a second complementary region of a second nucleic acid tag. Bridging polynucleotides may be partially or completely single stranded, including partially single stranded and partially double stranded.

A bridging nucleic acid may "bridge" two or more polynucleotides to form a polynucleotide complex. As used herein, the terms "polynucleotide", "oligonucleotide" and "nucleic acid" are used interchangeably. In some instances, a bridging polynucleotide may hybridize with two polynucleotide termini, including termini of the same or different nucleic acids, such that the termini are adjacent within the polynucleotide complex, e.g., allowing for the ligation of the adjacent termini. In some instances, a bridging polynucleotide may hybridize with two polynucleotide termini, including termini of the same or different nucleic acids, such that the termini are not adjacent in the resulting polynucleotide complex, e.g., are not adjacent such that they cannot be directly ligated together. In some instances, e.g., where two termini of a polynucleotide complex are not adjacent, a splint polynucleotide may be hybridized in the space between the two termini such that the ends of the splint polynucleotide are located adjacent to one or more of the termini. The term "splint polynucleotide" or "splint nucleic acid" as used herein refers to a polynucleotide, which may generally be single stranded or partially single stranded and partially double stranded, which may be used to fill one or more gaps between two polynucleotide termini of a polynucleotide complex, e.g., those complexes formed by use of a bridging polynucleotide. In some instances, a splint polynucleotide may have complementarity to one or more portions of a bridging polynucleotide. In some instances, the termini of one or more polynucleotides adjacent to a splint polynucleotide may be ligated to the splint polynucleotide.

Amplification

Proximity ligation assays (PLA) leverage the amplification power of the polymerase chain reaction (PCR) by linking the presence of the target analytes to the production of a PCR amplicon (e.g., as defined herein) which can be detected down to several hundred molecules. Any convenient PLAs may be adapted for use in the subject methods.

An exemplary workflow for the subject Glyco-seq method is shown in FIG. 3. Cell lysate is treated via the "Click-it"

method to install biotin or other moiety of interest onto O-GlcNAc, followed by incubation with two antibody-DNA conjugates: one that binds the target protein, and one that binds biotin. The two binding events bring the DNA strands into close proximity where addition of a complementary bridging DNA and DNA ligase can join them together, generating a PCR amplicon that can be quantified by PCR. In some cases, where the pair of capture agents (e.g., antibodies) bind at nearby sites can the amplicon be constituted, thus leading to specific detection of O-GlcNAc on a glycosylated target protein of interest.

Upon formation of an amplicon, or a joined polynucleotide from which an amplicon may be formed, or an elongated polynucleotide from which an amplicon may be formed, the amplicon may be amplified to generate an amplification product. Any convenient method of amplification may be utilized in generating the amplification product, as described in more detail below, and may depend upon the particular polynucleotide complex formed and/or particular requirements of the overall detection assay. As the formation of the amplicon is dependent on glycosylated target protein-mediated binding of the first and second conjugates, the presence of the amplification product may be indicative of the presence of the glycosylated target protein and/or the amount of the glycosylated target protein in the sample.

In some instances, amplification may be performed by polymerase chain reaction (PCR). In representative PCR amplification reactions, the reaction mixture generally includes a template nucleic acid which is combined with one or more primers that are employed in the primer extension reaction, e.g., the PCR primers (such as forward and reverse primers employed in geometric (or exponential) amplification or a single primer employed in a linear amplification). As such, in some instances, the hybridized portions of the above described nucleic acid complexes may serve as "primer" for the amplification reaction. For example, in instances where linear amplification is employed a single free 3'-terminus of hybridized nucleic acid of an above described nucleic acid complex may serve as a primer for amplification. In some instances, one or more additional nucleic acids may be added to serve as primer in a formed nucleic acid complex. For example, in some instances two target protein-bound nucleic acid tags may be joined in a ligation reaction and two additional primers may be added to facilitate amplification of the newly ligated nucleic acid segment or template. In some instances, a single free 3'-terminus of hybridized nucleic acid of an above described nucleic acid complex may serve as a first primer and a second primer may be added to facilitate amplification.

Any oligonucleotide primers with which the template nucleic acid (hereinafter referred to as template DNA for convenience) is contacted will be of sufficient length to provide for hybridization to complementary template DNA under annealing conditions. The primers will generally be at least 6 bp in length, including but not limited to e.g., at least 10 bp in length, at least 15 bp in length, at least 16 bp in length, at least 17 bp in length, at least 18 bp in length, at least 19 bp in length, at least 20 bp in length, at least 21 bp in length, at least 22 bp in length, at least 23 bp in length, at least 24 bp in length, at least 25 bp in length, at least 26 bp in length, at least 27 bp in length, at least 28 bp in length, at least 29 bp in length, at least 30 bp in length, and may be as long as 60 bp in length or longer, where the length of the primers will generally range from 18 to 50 bp in length, including but not limited to, e.g., from about 20 to 35 bp in length. In some instances, the template DNA may be contacted with a single primer or a set of two primers (forward and reverse primers), depending on whether primer extension, linear or exponential amplification of the template DNA is desired. Methods of PCR that may be employed in the subject methods include but are not limited to those described in U.S. Pat. Nos. 4,683,202; 4,683,195; 4,800,159; 4,965,188 and 5,512,462, the disclosures of which are herein incorporated by reference.

In addition to the above components, a PCR reaction mixture produced in the subject methods may include a polymerase and deoxyribonucleoside triphosphates (dNTPs). The desired polymerase activity may be provided by one or more distinct polymerase enzymes. In many embodiments, the reaction mixture includes at least a Family A polymerase, where representative Family A polymerases of interest include, but are not limited to: *Thermus aquaticus* polymerases, including the naturally occurring polymerase (Taq) and derivatives and homologues thereof, such as Klentaq (as described in *Proc. Natl. Acad. Sci USA* (1994) 91:2216-2220, the disclosure of which is incorporated herein by reference in its entirety); *Thermus thermophilus* polymerases, including the naturally occurring polymerase (Tth) and derivatives and homologues thereof, and the like. In certain embodiments where the amplification reaction that is carried out is a high fidelity reaction, the reaction mixture may further include a polymerase enzyme having 3'-5' exonuclease activity, e.g., as may be provided by a Family B polymerase, where Family B polymerases of interest include, but are not limited to: *Thermococcus litoralis* DNA polymerase (Vent) (e.g., as described in Perler et al., *Proc. Natl. Acad. Sci. USA* (1992) 89:5577, the disclosure of which is incorporated herein by reference in its entirety); *Pyrococcus* species GB-D (Deep Vent); *Pyrococcus furiosus* DNA polymerase (Pfu) (e.g., as described in Lundberg et al., *Gene* (1991) 108:1-6, the disclosure of which is incorporated herein by reference in its entirety), *Pyrococcus woesei* (Pwo) and the like. Generally, the reaction mixture will include four different types of dNTPs corresponding to the four naturally occurring bases are present, i.e. dATP, dTTP, dCTP and dGTP and in some instances may include one or more modified nucleotide dNTPs.

A PCR reaction will generally be carried out by cycling the reaction mixture between appropriate temperatures for annealing, elongation/extension, and denaturation for specific times. Such temperature and times will vary and will depend on the particular components of the reaction including, e.g., the polymerase and the primers as well as the expected length of the resulting PCR product. In some instances, e.g., where nested or two-step PCR are employed the cycling-reaction may be carried out in stages, e.g., cycling according to a first stage having a particular cycling program or using particular temperature(s) and subsequently cycling according to a second stage having a particular cycling program or using particular temperature(s).

In some instances, amplification may be carried out under isothermal conditions, e.g., by means of isothermal amplification. Methods of isothermal amplification generally make use of enzymatic means of separating DNA strands to facilitate amplification at constant temperature, such as, e.g., strand-displacing polymerase or a helicase, thus negating the need for thermocycling to denature DNA. Any convenient and appropriate means of isothermal amplification may be employed in the subject methods including but are not limited to: loop-mediated isothermal amplification (LAMP), strand displacement amplification (SDA), helicase-dependent amplification (HDA), nicking enzyme amplification reaction (NEAR), and the like. LAMP generally utilizes a plurality of primers, e.g., 4-6 primers, which may recognize a plurality of distinct regions, e.g., 6-8 distinct regions, of target DNA. Synthesis is generally initiated by a strand-displacing DNA polymerase with two of the primers forming loop structures to facilitate subsequent rounds of amplification. LAMP is rapid and sensitive. In addition, the magnesium pyrophosphate produced during the LAMP amplification reaction may, in some instances be visualized without the use of specialized equipment, e.g., by eye. SDA generally involves the use of a strand-displacing DNA polymerase (e.g., Bst DNA polymerase, Large (Klenow) Fragment polymerase, Klenow Fragment (3'-5' exo-), and the like) to initiate at nicks created by a strand-limited restriction endonuclease or nicking enzyme at a site contained in a primer. In SDA the nicking site is generally regenerated with each polymerase displacement step, resulting in exponential amplification. HDA generally employs: a helicase which unwinds double-stranded DNA unwinding to separate strands; primers, e.g., two primers, that may anneal to the unwound DNA; and a strand-displacing DNA polymerase for extension. NEAR generally involves a strand-displacing DNA polymerase that initiates elongation at a nicks, e.g., created by a nicking enzyme. NEAR is rapid and sensitive, quickly producing many short nucleic acids from a target sequence.

In some instances, entire amplification methods may be combined or aspects of various amplification methods may be recombined to generate a hybrid amplification method. For example, in some instances, aspects of PCR may be used, e.g., to generate the initial template or amplicon or first round or rounds of amplification, and an isothermal amplification method may be subsequently employed for further amplification. In some instances, an isothermal amplification method or aspects of an isothermal amplification method may be employed, followed by PCR for further amplification of the product of the isothermal amplification reaction.

In some instances, the amplification step and the detection step, described below, may be combined. In some instances, the particular amplification method employed allows for the qualitative detection of amplification product, e.g., by visual inspection of the amplification reaction with or without a detection reagent. In one embodiment, target protein-bound nucleic acid complex is amplified by isothermal amplification, e.g., LAMP, and the amplification generates a visual change in the amplification reaction indicative of efficient amplification and thus presence of the glycosylated target protein in the sample. In some instances, the amplification and detection steps are combined by monitoring the amplification reaction during amplification such as is performed in, e.g., real-time PCR (RT-PCR), also referred to herein as quantitative PCR (qPCR), and described in more detail below.

In some instances, the methods described herein may make use of those methods, e.g., amplification methods, and components thereof, employed in proximity ligation assays (PLA) and proximity elongation assays (PEA) including but not limited to, e.g., rolling circle amplification (RCA), binding-induced DNA assembly (BINDA), nicking enzyme assisted fluorescence signal amplification (NEFSA), and, e.g., those described in Janssen et al. (2013) *Sensors*, 13, 1353-1384, the disclosure of which is incorporated herein by reference in its entirety.

Detection

A variety of technologies are available to detect nucleic acid products which may be adapted for use in the subject methods. In some cases, fluorescence-based quantitative PCR (qPCR) may be used for high-throughput detection of DNA and RNA. The present disclosure provides an analytical platform that harnesses the power and ease of qPCR to detect glycosylation on a protein of interest. This method, which is termed herein Glyco-seq, makes use of "Click-it" labeling and proximity ligation assay and provides for detection of O-GlcNAc on proteins of interest by PCR. The subject methods can provide for the highly sensitive, multiplexed detection of O-GlcNAcylated proteins from cell lysate without enrichment while using accessible, affordable, and familiar qPCR equipment and reagents.

The presence of the amplification product may be determined, including qualitatively determined or quantitatively determined, by any convenient method. In some instances, the presence of the amplification product may be qualitatively determined, e.g., through a physical change in the amplification reaction that is indicative of efficient amplification of the target polynucleotide complex.

In some instances, the amplification product is detected and/or the amount of amplification product is measured by a detection protocol for non-specific detection of the amplified nucleic acid or a protocol for specific detection of the amplified nucleic acid. Representative non-specific detection protocols of interest include protocols that employ signal producing systems that selectively detect double stranded nucleic acid products, e.g., via intercalation. Representative detectable molecules that find use in such embodiments include fluorescent nucleic acid stains, such as phenanthridinium dyes, including monomers or homo- or heterodimers thereof, that provide enhanced fluorescence when complexed with nucleic acids. Examples of phenanthridinium dyes include ethidium homodimer, ethidium bromide, propidium iodide, and other alkyl-substituted phenanthridinium dyes. In another embodiment, a nucleic acid stain includes an acridine dye, or a homo- or heterodimer thereof, such as acridine orange, acridine homodimer, ethidium-acridine heterodimer, or 9-amino-6-chloro-2-methoxyacridine. In yet another embodiment, the nucleic acid stain is an indole or imidazole dye, such as Hoechst 33258, Hoechst 33342, Hoechst 34580, DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). In certain embodiments of the invention, the nucleic acid stain is a cyanine dye or a homo- or heterodimer of a cyanine dye that gives an enhanced fluorescence when associated with nucleic acids. In some instances, dyes described in U.S. Pat. Nos. 4,883,867, 5,582,977, 5,321,130, and 5,410,030, which are incorporated herein by reference in their entirety, may be used, including nucleic acid stains commercially available under the trademarks TOTO, BOBO, POPO, YOYO, TO-PRO, BO-PRO, PO-PRO and YO-PRO (Life Technologies, Inc. Grand Island, N.Y.). In some instances, dyes described in U.S. Pat. Nos. 5,436,134, 5,658,751 and 5,863,753, which are incorporated herein by reference in their entirety, may be used, including nucleic acid stains commercially available under the trademarks SYBR, SYTO, SYTOX, PICOGREEN, OLIGREEN, and RIBOGREEN (Life Technologies, Inc. Grand Island, N.Y.). In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives enhanced fluorescence when associated with nucleic acids, including nucleic acid stains commercially available under the trademarks SYTO, SYTOX, JOJO, JO-PRO, LOLO, LO-PRO (Life Technologies, Inc. Grand Island, N.Y.).

In yet other embodiments, a signal producing system that is specific for the amplification product, as opposed to double stranded molecules in general, may be employed to detect the amplification. In these embodiments, the signal producing system may include a probe nucleic acid that specifically binds to a sequence found in the amplification product, where the probe nucleic acid may be labeled with a directly or indirectly detectable label. A directly detectable label is one that can be directly detected without the use of additional reagents, while an indirectly detectable label is one that is detectable by employing one or more additional reagent, e.g., where the label is a member of a signal producing system made up of two or more components. In some embodiments, the label is a directly detectable label, where directly detectable labels of interest include, but are not limited to: fluorescent labels, radioisotopic labels, chemiluminescent labels, and the like. In some embodiments, the label is a fluorescent label, where the labeling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labeled probe nucleic acids include, but are not limited to: fluorescein, the cyanine dyes, such as Cy3, Cy5, Alexa 555, Bodipy 630/650, and the like. Other labels, such as those described above, may also be employed.

In those embodiments where the signal producing system is a fluorescent signal producing system, signal detection in some cases includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, and in certain embodiments is an increase in fluorescence. The sample may be screened for an increase in fluorescence using any convenient means, e.g., a suitable fluorimeter, such as a thermostable-cuvette or plate-reader fluorimeter. Fluorescence is suitably monitored using a known fluorimeter. The signals from these devices, for instance in the form of photo-multiplier voltages, are sent to a data processor board and converted into a spectrum associated with each sample tube. Multiple reaction vessels, e.g., multiple tubes, multi-well plates, etc., can be assessed at the same time.

In some instances, the elongation and/or amplification of a particular polynucleotide of a nucleic acid complex, e.g., a target protein-bound nucleic acid complex, a bridging polynucleotide, a circularizing oligonucleotide, etc., results in the duplication of one or more specific nucleic acid sequences resulting in one or more strands containing repeats of the one or more specific nucleic acid sequences. Such repetitive sequences may be detected, e.g., through hybridization of a probe nucleic acid specific for the repeated specific sequence. In certain instances, a tagged probe nucleic acid, e.g., a fluorescently tagged probe nucleic acid, an enzymatically tagged probe nucleic acid, a radiolabel tagged probe nucleic acid, etc., specific for the repeated specific sequence may be utilized to detect an elongated polynucleotide or amplification product that contains the repeated specific sequence. In some instances, hybridization of a tagged probe nucleic acid to a repeating sequence of an elongated polynucleotide or amplification product allows for the detection of the elongated polynucleotide or amplification product due to the high number of tagged probe nucleic acids hybridized to the elongated polynucleotide or amplification product, which results in a high local concentration of detectable tag.

For example, in some instances, repeats of one or more sequences of a target protein-bound nucleic acid complex are contained in an amplification product or elongation product produced according to the methods described herein and the repeats are detected through the use of a tagged probe nucleic acid specific for the repeating sequence units. In some instances, repeats of one or more sequences of a bridging polynucleotide are contained in an amplification product or elongation product produced according to the methods described herein and the repeats are detected through the use of a tagged probe nucleic acid specific for the repeating sequence units. In some instances, repeats of one or more sequences of a circularizing oligonucleotide are contained in an amplification product or elongation product produced according to the methods described herein and the repeats are detected through the use of a tagged probe nucleic acid specific for the repeating sequence units.

In certain embodiments, a repeating nucleic acid sequence may be produced by one or more of the elongation and/or amplification methods described herein, e.g., PCR amplification, isothermal amplification (e.g., RCA), etc., and the elongation and/or amplification product may be made detectable through hybridization of one or more fluorescently labeled probe nucleic acid to the elongation and/or amplification product. Such detectable elongation and/or amplification product may be identified through any convenient means for detecting fluorescence, including but not limited to, e.g., fluorescent microscopy, flow cytometry, imaging flow cytometry, etc. In some instances, identification of a detectable elongation and/or amplification product may allow for detection or identification of a molecule, particle, cell, tissue, organism, etc., associated with the antigen binding agent of the complex from which the elongation and/or amplification product was derived. For example, in some instances, fluorescent probe-bound elongation and/or amplification product may remain associated with a cell that produced the antigen binding agent allowing identification of the cell, e.g., by fluorescent microscopy, and/or isolation of the cell, e.g., by fluorescent activated cell sorting (FACS).

As noted above, in some instances, amplification may be monitored in real time to provide detection and/or quantitation. Where the detection protocol is a real time protocol, e.g., as employed in RT-PCR or qPCR reaction protocols, data may be collected at frequent intervals, for example once every 10 milliseconds (ms), or more or less frequently than once every 10 ms, throughout the reaction. By monitoring the fluorescence of the reactive molecule from the sample during each cycle, the progress of the amplification reaction can be monitored in various ways. For example, the data provided by melting peaks can be analyzed, for example by calculating the area under the melting peaks and these data plotted against the number of cycles.

The spectra generated in this way can be resolved, for example, using "fits" of pre-selected fluorescent moieties such as dyes, to form peaks representative of each signaling moiety (i.e. fluorophore). The areas under the peaks can be determined which represents the intensity value for each signal, and if required, expressed as quotients of each other. The differential of signal intensities and/or ratios will allow changes in labeled probes to be recorded through the reaction or at different reaction conditions, such as temperatures. The changes are related to the binding phenomenon between the oligonucleotide probe and the target sequence or degradation of the oligonucleotide probe bound to the target sequence. The integral of the area under the differential peaks will allow intensity values for the label effects to be calculated.

Screening the mixture for a change in fluorescence provides one or more assay results, depending on whether the sample is screened once at the end of the amplification reaction, or multiple times during the reaction, e.g., after each cycle (e.g., as is done in RT-PCR monitoring).

According to the methods described herein, the presence of glycosylated target protein may be detected, e.g., as above or below a particular detection threshold, or may be measured, e.g., the actual amount or concentration of the glycosylated target protein in the sample may be measured when present above a particular detection threshold. The actual detection threshold for a subject glycosylated target protein detection reaction will vary and will depend on, e.g., the glycosylated target protein to be detected the particular amplification method employed, the detection method employed, and the like. In some instances, the detection threshold for the subject detection methods may range from 15 ng/ml to 1 pg/ml and may include less than 15 ng/ml, less than 14 ng/ml, less than 13 ng/ml, less than 12 ng/ml, less than 11 ng/ml, less than 10 ng/ml, less than 9 ng/ml, less than 8 ng/ml, less than 7 ng/ml, less than 6 ng/ml, less than 5 ng/ml, less than 4 ng/ml, less than 3 ng/ml, less than 2 ng/ml, less than 1 ng/ml, less than 500 pg/ml, less than 400 pg/ml, less than 300 pg/ml, less than 200 pg/ml, less than 100 pg/ml, less than 90 pg/ml, less than 80 pg/ml, less than 70 pg/ml, less than 60 pg/ml, less than 50 pg/ml, less than 40 pg/ml, less than 35 pg/ml, less than 30 pg/ml, less than 25 pg/ml, less than 20 pg/ml, less than 19 pg/ml, less than 18 pg/ml, less than 17 pg/ml, less than 16 pg/ml, less than 15 pg/ml, less than 14 pg/ml, less than 13 pg/ml, less than 12 pg/ml, less than 10 pg/ml, etc. In some instances, the detection threshold for a particular detection method described herein may be expressed in the minimum moles of glycosylated target protein that may be detected in a sample and, such detection thresholds may range from 200 attomoles to 100 zeptomoles, including but not limited to e.g., 200 attomoles, 190 attomoles, 180 attomoles, 170 attomoles, 160 attomoles, 150 attomoles, 140 attomoles, 130 attomoles, 120 attomoles, 110 attomoles, 100 attomoles, 90 attomoles, 80 attomoles, 70 attomoles, 60 attomoles, 50 attomoles, 40 attomoles, 30 attomoles, 20 attomoles, 10 attomoles, 1 attomole, 900 zeptomoles, 800 zeptomoles, 700 zeptomoles, 600 zeptomoles, 500 zeptomoles, 400 zeptomoles, 350 zeptomoles, 300 zeptomoles, 250 zeptomoles, 200 zeptomoles, 190 zeptomoles, 180 zeptomoles, 170 zeptomoles, 160 zeptomoles, 150 zeptomoles, 140 zeptomoles, 130 zeptomoles, 120 zeptomoles, 110 zeptomoles, 100 zeptomoles, etc.

Following detection, which may or may not include qualitative or quantitative measurement of the amplification product, the result of the detection may be assessed to determine the likelihood that the glycosylated target protein is present in the sample. In making such assessments, in some instances, the subject reaction may be compared to one or more control reactions or reference values. Control reactions of the subject method include positive controls, e.g., a sample known to contain the target protein of interest and/or known to contain a known amount of target protein of interest and/or known to have a particular level of glycosylation. Control reactions may also include negative controls, e.g., samples known to not contain a critical component, e.g., the target protein, glycosylated target protein, the polymerase, a critical polynucleotide, etc. Reference values to which results of a detection reaction may be compared include but are not limited to a reference measurement from any control reaction performed previously, a standard curve gathered from a control reaction, a set of measured fluorescent values from positive or negative controls, user-defined reference values, manufacturer supplied reference values, etc. In some instances, assessment of a subject reaction may include comparison to a scale, e.g., a scale of reference values, which can be used to estimate the amount of antigen binding agent present in the sample.

The subject methods may be used in glycoproteomics to deconvolute the relative signal contributions from changes in target protein abundance versus changes in the amount of O-GlcNAc present on the protein. In other methods, an increase in signal detected from O-GlcNAc could reflect for instance an increase in the modification present per protein, or a simple increase in the protein abundance with no change in the modification stoichiometry. The subject Glyco-seq methods are well equipped to monitor these two parameters independently. Changes in protein abundance may be monitored side-by-side with changes in O-GlcNAc stoichiometry, and therefore the O-GlcNAc present on proteins of interest can be quantified.

Multiplexing

According to the methods described herein, a sample is readily screened for the presence of glycosylated target protein. The methods are suitable for detection of a single glycosylated target protein as well as multiplex analyses, in which two or more different glycosylated target protein are assayed in the sample. In these latter multiplex situations, the number of different sets of first and second conjugates and bridging nucleic acids that may be employed typically ranges from about 2 to about 20 or higher, e.g., as up to 100 or higher, 1000 or higher, etc. In one embodiment, a multiplexed assay may make use of various different capture agents conjugated to unique nucleic acid tags (i.e., conjugates, as described herein) in conjunction with bridging nucleic acids such that amplification of a particularly unique amplicon is indicative of the presence of the associated glycosylated target protein. Accordingly, the subject assays may make use of nucleic acid tagging and/or "barcoding" strategies to allow for the detection and/or quantification of a plurality of glycosylated target proteins in a sample. The number of different first and second conjugates, uniquely tagged with nucleic acid barcodes, that may be included in a multiplexed assay as described herein may vary and may be limited only by, e.g., the available length of polynucleotide in the first and second conjugates for the barcode, the physical limit of conjugate concentration that may be present in the reaction without negatively impacting the specific binding to the target protein and/or polynucleotide binding, and the like.

As such, in some instances, a panel of glycosylated target proteins may be screened in a single reaction and the presence, quantities or level of glycosylation of each glycosylated target protein on the panel may be assessed. The detection methods described above may be utilized in parallel for the detection and measurement of amplification products in a duplexed assay. In some instances, in both multiplexed and non-multiplexed assays, nucleic acid sequencing methods may be utilized for detection and/or measurement of amplification product. For example, in some instances, quantitative sequencing may be utilized, e.g., in a multiplexed assay having produced a plurality of amplification products, to determine the relative amounts or presence of each amplification product allowing for a highly sensitive and highly multiplexed assessment of many different glycosylated target proteins in a single sample.

Aspects of the present disclosure also include methods for detecting a low-abundance protein in a biological sample. The phrase "low-abundance protein", as used herein, refers to one or more proteins (e.g., glycosylated proteins) present in a sample in a sufficiently low quantity that they may be difficult to detect by some methods (e.g., LC-MS/MS approaches that select only the most intense ions in a given sample for fragmentation and/or further analysis). Low abundance proteins (e.g., low abundance glycosylated proteins) have a concentration that is less than that of high abundance proteins. For example, low abundance proteins may have a concentration of less than 100 ng/mL, such as less than 75 ng/mL, such as less than 50 ng/mL and including less than 25 ng/mL in a biological sample. In other embodiments low abundance proteins are present in a biological sample containing a mixture of proteins in an amount that is less than or equal to 1000 pg/mg of total protein in the biological sample, such as 750 pg/mg, such as 500 pg/mg and including equal to or less than 250 pg/mg of total protein in the biological sample. In certain instances, methods of the present disclosure include detecting and identifying low abundance proteins in a biological sample present in an amount that is equal to or less than 100 pg/mg of total protein, less than 50 pg/mg of total protein, or less than 10 pg/mg total protein.

Determining the Level of Total Target Protein

In any of the above-described embodiments, a method of the present disclosure can further include a step of detecting total target protein (total target protein, including unglycosylated target protein and glycosylated target protein).

For example, in some cases, a capture agent that binds the target protein (e.g., that binds an epitope comprising a stretch of amino acids, such as from 2 amino acids to 20 amino acids) can be used to determine the amount of total target protein. In some cases, the same capture agent that is used in the first conjugate, described above, can be used to determine the level of total target protein. In some cases, the capture agent that is used in the first conjugate, described above, is different from the capture agent(s) used to determine the level of total target protein.

Proximity Ligation Assays

In some cases, determining the amount of total target protein is carried out using a proximity-based ligation assay comprising: (a) contacting the sample with: (i) a third conjugate comprising a third nucleic acid tag linked to a third capture agent that specifically binds a first epitope in the target protein; (ii) a fourth conjugate comprising a fourth nucleic acid tag linked to a fourth capture agent that specifically a second epitope in the target protein; and (iii) a bridging nucleic acid that hybridizes to the third and fourth nucleic acid tags; under conditions sufficient to specifically bind the third and fourth capture agents to the probe-labeled target protein and to hybridize the bridging nucleic acid to the third and fourth nucleic acid tags to produce a target protein-bound nucleic acid complex; and (b) detecting the target protein-bound nucleic acid complex.

In some cases, the third capture agent and the fourth capture agents are antibodies that recognize distinct epitopes on the target protein. Suitable nucleic acid tags are as described above. Suitable PCR-based detection methods are as described above.

Where detection of the total target protein and detection of glycosylated target protein are both carried out using a proximity ligation assay, detection of total target protein and detection of glycosylated target protein can be carried out in the same reaction vessel. Where detection of the total target protein and detection of glycosylated target protein are both carried out using a proximity ligation assay, detection of total target protein and detection of glycosylated target protein can be carried out in two separate reaction vessels.

In some cases, the amount of total target protein is compared to the amount of glycosylated target protein, such that a ratio of glycosylated target protein to total target protein is obtained. In some cases, the amount of glycosylated target protein and the amount of total target protein are determined over time, e.g., in response to a stimulus.

Immunological Assays

For example, in some cases, the first capture agent is an antibody that specifically binds a protein epitope in the target protein. The total amount of target protein can be determined using a detectably labeled antibody that specifically binds a protein epitope in the target protein. In some cases, the antibody is the same as the first capture agent. The amount of total target protein can be determined using, e.g., an immunological assay, where suitable immunological assays include, e.g., an enzyme-linked immunosorbent assay (ELISA), a radioimmunoassay (RIA), and the like.

In some cases, the step of detecting or determining the total target protein comprises contacting the sample with a detectably labeled antibody that specifically binds a protein epitope in the target protein; forming a complex between the detectably labeled antibody and the target protein in the sample; and determining the amount of total target protein based on the amount of detectably labeled antibody in the complex. Suitable detectable labels include, e.g., radioisotopes; enzymes that generate fluorescent products, luminescent products, or colored products; fluorescent proteins; fluorescent dyes; and the like.

In some cases, the amount of total target protein is compared to the amount of glycosylated target protein, such that a ratio of glycosylated target protein to total target protein is obtained. In some cases, the amount of glycosylated target protein and the amount of total target protein are determined over time, e.g., in response to a stimulus.

Utility

The methods and compositions described herein have particular utility in the detection and/or quantification of a glycosylated target protein present in a sample. Such detection may find various applications in a variety of technological fields including but not limited to e.g., basic scientific research (e.g., biomedical research, biochemistry research, immunological research, molecular biology research, microbiological research, cellular biology research, genetics, and the like), medical and/or pharmaceutical research (e.g., drug discovery research, drug design research, drug development research, pharmacology, toxicology, medicinal chemistry, pre-clinical research, clinical research, personalized medicine, and the like), medicine, epidemiology, public health, biotechnology, veterinary science, veterinary medicine, agriculture, material science, molecular detection, molecular diagnostics, and the like.

In some instances, methods described herein find use in detection of glycosylated target protein in a biological sample from a subject. The term "subject" as used herein refers to an animal, including humans, livestock, pets, laboratory animals, bioproduction animals (e.g., animals used to generate a bioproduct, e.g., an antibody), and the like. In some instances, a sample is derived from a mammalian subject, including e.g., mammalian tissue, mammalian cells, mammalian bodily fluid, mammalian excreted bodily fluids, mammalian semi-solid secretions, and the like.

Compositions

Aspects of the present disclosure include compositions, e.g., reagents and kits, useful in practicing the methods described herein. Any of the composition components described herein may find use individually in a method or kit for detecting glycosylate target proteins. For example, the present disclosure provides first and second conjugates useful in the described detection methods.

In some embodiments, the composition includes (a) a first conjugate including a first nucleic acid tag linked to a first capture agent (e.g., as described herein) that is capable of specifically binding a target protein; and (b) a second conjugate including a second nucleic acid tag linked to a second capture agent (e.g., as described herein) that is capable of specifically binding a probe. The compositions may further include a bridging nucleic acid that is complementary to the first and second nucleic acid tags (e.g., as described herein). The composition may further includes a probe-labeled glycosylated target protein (e.g., as described herein).

Kits

In yet another aspect, the present disclosure provides kits for practicing the subject methods, e.g., as described above. The subject kits may include any combination of the herein described reagents, or compositions useful in practicing the methods as described above including but not limited to, e.g., one or more of the described first and second conjugates, bridging polynucleotides, splint polynucleotides, reactive probes, enzymatic reagents (e.g., ligases), and the like. Subject kits may further include one or more reagent preparation reagents including but not limited to, e.g., reagents for labelling an metabolically tagged target protein, reagents for functionalizing a polynucleotide, reagents for conjugation of a polynucleotide and/or a capture agent. In addition, subject kits may further include assay reagents or reagents useful in performing an assay of a sample, e.g., a patient sample, to allow for an assessment, e.g., of whether one or more glycosylated target proteins are present in a sample from the subject. Such assay reagents may include but are not limited to, e.g., detection reagents, sample preparation reagents, amplification reagents (e.g., PCR reagents and/or isothermal amplification reagents and/or qPCR reagents, etc.) and binding reagents (e.g., conjugates, and the like), buffers, diluents, etc. Such assay kits may further include sample collection components, e.g., sample collection containers and/or sample collection devices, etc. The above components may be present in separate containers or one or more components may be combined into a single container, e.g., a glass or plastic vial or tube.

Kits may further include control reagents and samples including but not limited to, e.g., control samples (e.g., positive control samples, negative control samples, etc.) calibration reagents (e.g., fluorescent calibration reagents, etc.).

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, removable drive (e.g., flash memory device), etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Glyco-Seq to Detect O-GlcNAcylation State of a Target Protein

Figure 4:
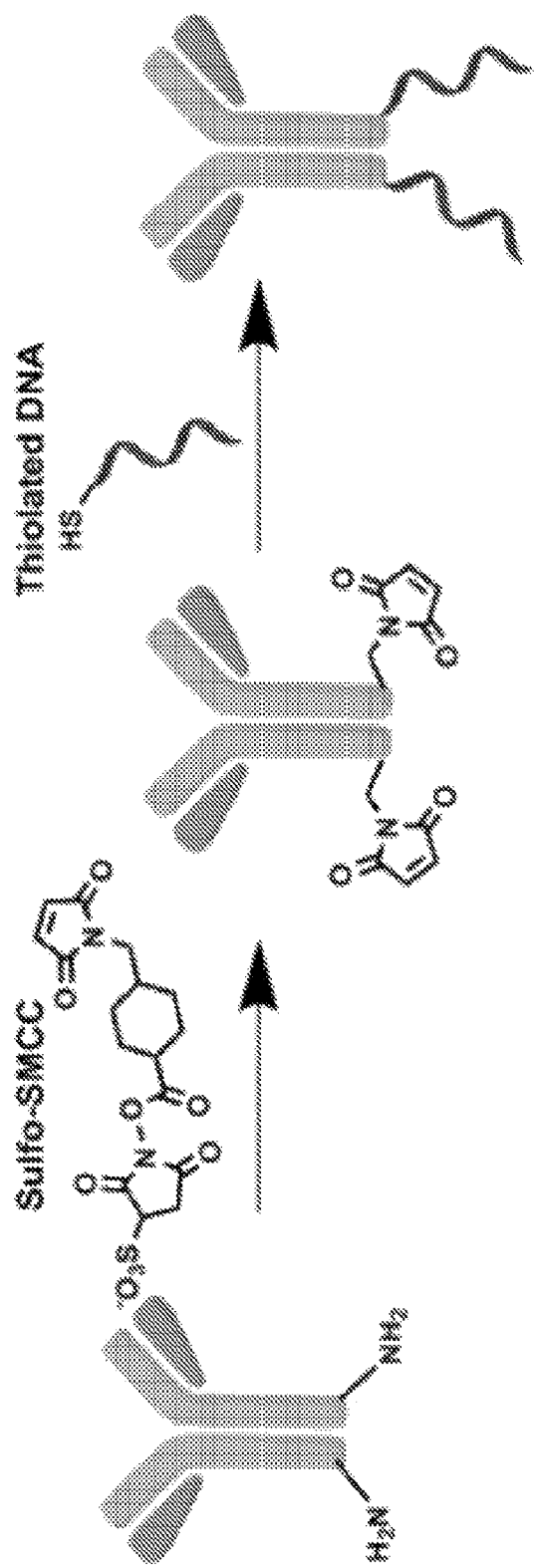
FIG. 4 illustrates the synthesis of antibody-DNA conjugates via succinimidyl 4-[N-maleimidomethyl]-cyclohexane-1 carboxylate (SMCC) crosslinking.

Design and Synthesis of Reagents for Detection of O-GlcNAc by Proximity Ligation There are many published protocols that are suitable for proximity ligation. In preliminary experiments, succinimidyl 4-[N-maleimidomethyl]-cyclohexane-1 carboxylate (SMCC) crosslinking reagent was used for generating antibody-DNA conjugates (FIG. 4). SMCC is a lysine-to-sulfhydryl crosslinker. The succinimidyl ester reacts with lysine residues on the antibody to attach maleimide groups for later functionalization with thiolated oligonucleotides. The thiolated oligonucleotides used in proximity ligation assay (PLA) are approximately 50 base pairs in length. The SMCC crosslinker is a scaleable reagent used in the preparation of antibody conjugations. The covalent conjugation of DNA to several antibodies using SMCC was confirmed by a mass shift on sodium dodecyl sulfate-polyacrylamide gel electrophoresis (SDS-PAGE) gel. Excess DNA was used, and the conjugate was purified to remove the excess DNA. The DNA:antibody ratio was on average 2.5 oligos per antibody as determined by UV-VIS. These syntheses were performed on a 20 μg scale with a ~50% yield, providing enough reagent for ca. 30,000 assays. Several conjugation strategies were screened to achieve a combination of high yield, ease, affordability, and reproducibility for these reagents.

Use of Glyco-Seq to Detect O-GlcNAc on Recombinant and Endogenous Proteins

The antibody-DNA conjugates are used to detect O-GlcNAc on purified proteins using a Glyco-seq method. Alpha crystallin (Ac), a bovine protein with low levels of O-GlcNAc modification is analyzed. The protein is subjected to "Click-it" conditions to append biotin onto O-GlcNAc, and then treated with two antibody-DNA conjugates: one directed against biotin the other directed against Ac itself. Upon treatment with a bridging DNA (which is ca. 20 base pairs in length) and ligase, and PCR amplification and detection of DNA using a SYBR green-based qPCR kit, a signal resulting from amplified DNA is observed. The above described experiments were performed on purified Ac. Purified protein was also added to lysate to test the detection capability of the method in a more complex environment as shown in FIG. 5A-5B.

Several types of control experiments are also performed. The purified protein is treated with OGA to cleave off the O-GlcNAc, or with heat-deactivated OGA. Signal only results from the sample that still retains O-GlcNAc. Also, a parallel experiment is performed in which Ac is treated with a second antibody-DNA conjugate targeted towards the Ac protein, instead of the anti-biotin conjugate. This latter set of conjugates is designed to detect the protein itself, and produces signal irrespective of treatment with OGA.

Figure 5:
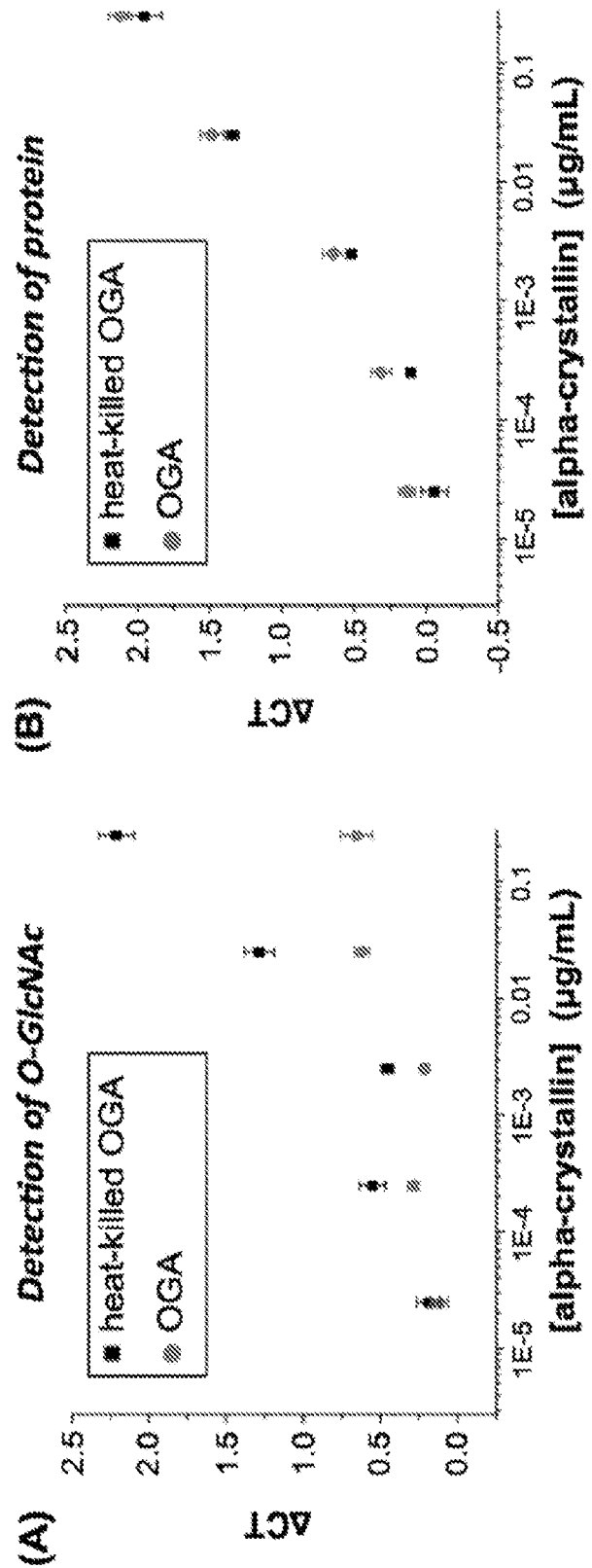
FIG. 5A-5B show the results of detection of O-GlcNAc in a complex sample. Alpha-crystallin (Ac) was treated with either OGA or heat-killed OGA, and then added the Ac into cell lysate at 1% wt, and detected either for O-GlcNAc (A) or total protein level (B) using Glyco-seq. (A) OGA treated sample shows a significantly weak signal due to the loss of O-GlcNAc. (B) Both samples showed strong signal for total protein level. This result demonstrates that the observed signal difference in (A) was due to differential O-GlcNAc levels. (ΔCT: change in cycle threshold; a conventional means of reporting qPCR signal relative to a control sample).
Figure 6:
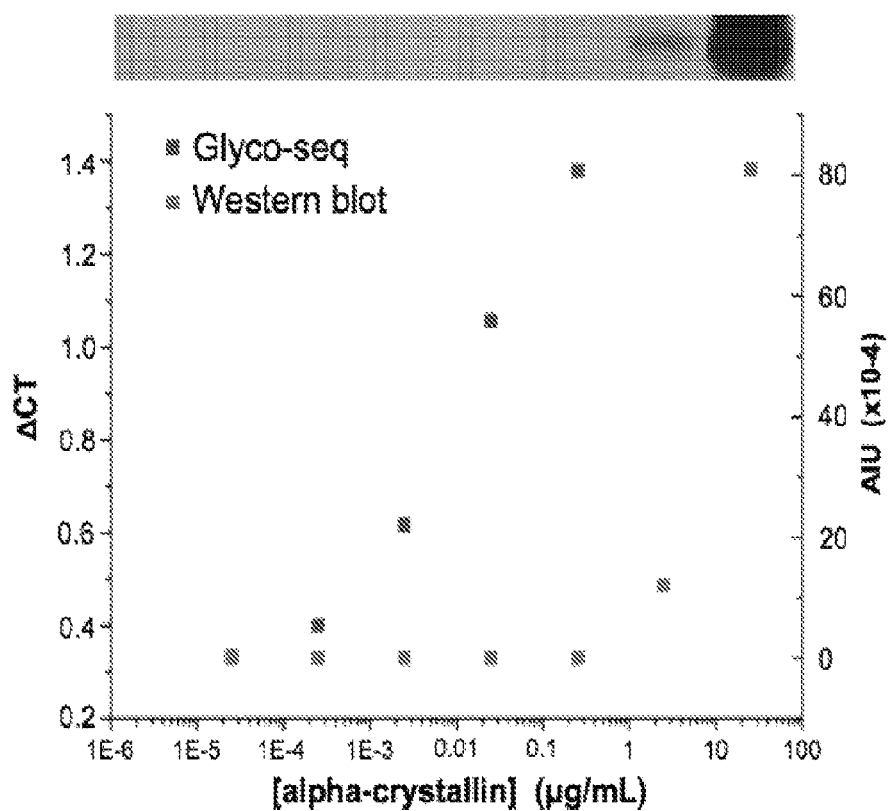
FIG. 6 shows a graphic comparison of Glyco-seq versus Western blot. Glyco-seq signal is reported as ΔCT as described in FIG. 5A-5B. Western blotting was performed using streptavidin-HRP.

FIG. 5A-5B: Detection of O-GlcNAc in a complex environment. Alpha-crystallin (Ac) was treated with either OGA or heat-killed OGA, and then added into cell lysate at 1% wt, and detected either O-GlcNAc (A) or total protein level (B) by Glyco-seq. FIG. 5A. OGA treated sample shows a significantly weak signal due to the loss of O-GlcNAc. In FIG. 5B, both samples showed strong signal when total protein level was detected. This result verifies that the observed signal difference in (A) was due to differential O-GlcNAc levels. (ΔCT: change in cycle threshold; a standard means of reporting qPCR signal relative to a control sample). The results illustrated in FIG. 5A-5B demonstrate that Glyco-seq may be used for the protein-specific detection of O-GlcNAc. The purified Ac was added to lysate to evaluate the detection capability in a more complex environment as shown in FIG. 5A-5B. In was observed that very little sample was required to detect signal over background. In order to benchmark the sensitivity of this technique versus other analytical strategies, a proximity ligation assay was performed in parallel with an anti-biotin Western blot assay directed against the Ac sample which had been treated via "Click-it" (FIG. 6). FIG. 6 shows a comparison of Glyco-seq versus Western blot. Glyco-seq signal is reported as ΔCT as described in FIG. 5A-5B. Western blotting was performed with streptavidin-HRP. In this experiment, O-GlcNAcylation was detected via Glyco-seq down to 0.1 fmol of protein. This is 104-fold more sensitive than what was observed via Western blotting, which required 1 pmol of sample. This sensitivity is highly advantageous for reduced sample consumption and ease of detection for low-abundance targets.

Glyco-seq is applied to several other protein targets to demonstrate generalizability. The excellent sensitivity of Glyco-seq is harnessed to detect the O-GlcNAcylation state of transcription factors. O-GlcNAc is known to modify a number of transcription factors, and is thought to play a role in regulating their action. To evaluate the use of Glyco-seq, the protein c-Rel is analyzed according to the workflow described above. c-Rel is a low copy number transcription factor that alters expression of cytokine-encoding genes upon O-GlcNAcylation. The Glyco-seq reagents are used to detect endogenous c-Rel in Jurkat lysates. As a control, selective immunodepletion of c-Rel from the lysate is also be performed. The signal resulting from Glyco-seq diminishes as c-Rel is depleted.

To verify that the subject assay is accurately reporting changes in the amount of O-GlcNAcylation present on a target protein, several control experiments are performed. Cells are treated with Thiamet G, a known OGA inhibitor to check for an increase in O-GlcNAcylation on specific proteins. Treatment with Thiamet G prevents O-GlcNAc from being hydrolyzed from proteins, leading to an increase in detectable O-GlcNAcylation. The fold-changes observed from measurements using the subject methods to those found from other methods are compared. SILAC-based mass spectrometry has been used to report the changes of O-GlcNAcylation on about 30 protein targets, where the stoichiometry changes can be anywhere between 0.8-25 fold (Zachara et al., The dynamic stress-induced "O-GlcNAc-ome" highlights functions for O-GlcNAc in regulating DNA damage/repair and other cellular pathways. Amino Acids 2011, 40(3), 793-808). O-GlcNAcylation is quantified on target proteins from high to low fold changes including SEC24-C (23.8 fold), NF45 (4.3 fold), NUP153 (2.1 fold), NUP54 (1.5 fold) and OGT (1.0 fold). These studies establish the minimum fold-change that Glyco-seq can detect.

Example 2: Multiplexed Glyco-Seq as a Platform for the Detection of Protein O-GlcNAcylation The subject methods can be used to detect multiple target proteins at once (e.g., multiplexing). This is accomplished by using several pairs of first and second antibody-DNA conjugates, each directed at different target proteins. Each pair is prepared with unique DNA sequences incorporated into the first and second conjugates. Primer pairs that are designed to uniquely amplify each ligated pair of conjugates are used to achieve detection, e.g., via qPCR. In this manner, multiple targets are analyzed in a single experiment by simply performing the assay with a new set of primers. Multiplexing is performed in the context of Glyco-seq for the detection of O-GlcNAc.

Measuring Changes in Protein Abundance Versus Changes in O-GlcNAc

The subject methods find use in glycoproteomic investigations to differentiate an increase in detected glycosylation arising from an increase in the amount of glycosylation present on a protein, from an increase in the amount of the glycoprotein present in a sample. Changes in protein abundance can be detected using paired antibody-DNA conjugates that are both directed at the protein (e.g., to different protein epitopes). The amount of amplicon reconstituted by this ligation correlates with protein abundance. With appropriate standards and statistical power, by comparing the signal from the subject Glyco-seq experiment with the signal from such a PLA for protein detection, the O-GlcNAc present on proteins of interest is quantified. The subject method detects protein abundance in parallel with the amount of O-GlcNAc on the protein.

Assay to Detect Other Modifications and Quantify Changes in Modification

Sites of O-GlcNAc modification are often competitive with phosphorylation in what is often described as the "Yin-Yang" model (Groves et al., Dynamic O-GlcNAcylation and its roles in the cellular stress response and homeostasis. Cell Stress Chaperones 2013, 18(5), 535-55). The subject methods provide for the parallel detection of protein phosphorylation by incorporating an anti-phosphoserine or anti-phosphotyrosine antibody-DNA conjugate into the Glyco-seq workflow instead of the anti-biotin/DNA conjugate.

Antibody-DNA conjugates are prepared to provide for simultaneous detection of O-GlcNAc and phosphorylation on RNA polymerase-II, which serves many roles in cells including initiation of transcription and recruitment of the RNA processing machinery, and is reciprocally modified by these two Post-Translational Modifications (PTMs). These PTMs are monitored in lysates derived from cells that have and have not been subjected to stimuli that alter transcription. Comparing the data from both lysate sets reveals changes in O-GlcNAc levels, as well as changes in phosphorylation levels in response to the stimuli. In this manner, in one experiment it is observed how the amount of each modification on RNA polymerase-II changes in response to the same stimuli.

Multiplexed Assay with Model System of In Vitro Glycosylated Recombinant Proteins The subject assays are sensitive for the detection of low abundance proteins without enrichment. In addition, the subject assay includes the ability to detect changes in many proteins at once. Unique primer pairs are used to encode the identity of each protein in a multiplexed assay.

All antibody-DNA conjugates are present in the assay and ligated simultaneously using a single universal bridging DNA. Deconvolution is achieved by interrogating with different primer sets via qPCR. The strength of this strategy is underscored by the availability of inexpensive premade 96- and 384-well plates with dried primers. The ligated library pool is then partitioned into the many wells to interrogate up to 50 targets in a single experiment while only consuming a few ng of cell lysate.

To demonstrate Glyco-seq for the multiplexed detection of O-GlcNAc on several proteins, several purified model O-GlcNAcylated proteins are used as a model system for the subject multiplexed method. Rabbit reticulocyte lysate retains endogenous OGT activity and is commonly used as a method for the in vitro O-GlcNAcylation of proteins (Starr, C. M.; Hanover, J. A. Glycosylation of nuclear pore protein p62. Reticulocyte lysate catalyzes O-linked N-acetylglucosamine addition in vitro. J Biol Chem 1990, 265(12), 6868-73). The recombinant, unglycosylated proteins are mixed together in known concentrations and glycosylated with the reticulocyte lysate. The model set is analyzed using the subject multiplexed proximity ligation assay described herein, using proximity probes to detect both glycosylation and protein abundance. Using this master mix as a standard, the detection limit and reproducibility of the multiplexed proximity ligation assay is determined.

While the sequence diversity of oligonucleotides is immense, the scope of multiplexability is in practice limited by the orthogonality of the primer pairs and cross-reactivity of the DNA on antibody-DNA conjugates, which is determined empirically. To evaluate the primers, the unconjugated amplicons are mixed together in known quantities to create a standard. Next, qPCR is performed using each set of primers and the amplification efficiency and signal intensity compared to ensure that each set amplifies selectively and in a reproducible manner.

Multiplexed Glyco-Seq Assay to Detect Glycosylation of Transcription Factors

In this experiment, antibody-DNA conjugates are synthesized to monitor the O-GlcNAcylation of several transcription factors.

TABLE 1 selected transcription factors of interest that are O-GlcNAcylated.

| | |
|---|---|
| PDX-1 | PGC-1alpha |
| Neuro-D1 | ER-alpha |
| C-Rel | ER-beta |
| Sp1 | TORC2/CRTC2 |
| NFkB | NFATalpha1 |
| P53 | Elf-1 |
| Fox01 | c-myc |
| Oct4 | Pdx-1 |
| Sox2 | C/EBP beta |
| Stat5a | MafA |
| CREB | Id2 |
| YY1 | USF |

Select transcription factors from Table 1 are expressed and purified and glycosylated with reticulocyte lysate as described above to create external standards. Next, lysates are prepared by subjecting them to "Click-it" conditions to attach biotin on O-GlcNAc. One set of lysates is from cells stressed via hypoxia while another set is from untreated cells as a control. Using the standards, a multiplexed proximity ligation experiment is performed to compare the changes in O-GlcNAcylation to reported changes found in transcription factors (see e.g., Ferrer et al., O-GlcNAcylation regulates cancer metabolism and survival stress signaling via regulation of the HIF-1 pathway. Mol Cell 2014, 54(5), 820-31; and Lazarus et al., HCF-1 is cleaved in the active site of O-GlcNAc transferase. Science 2013, 342(6163), 1235-9).

Figure 7:
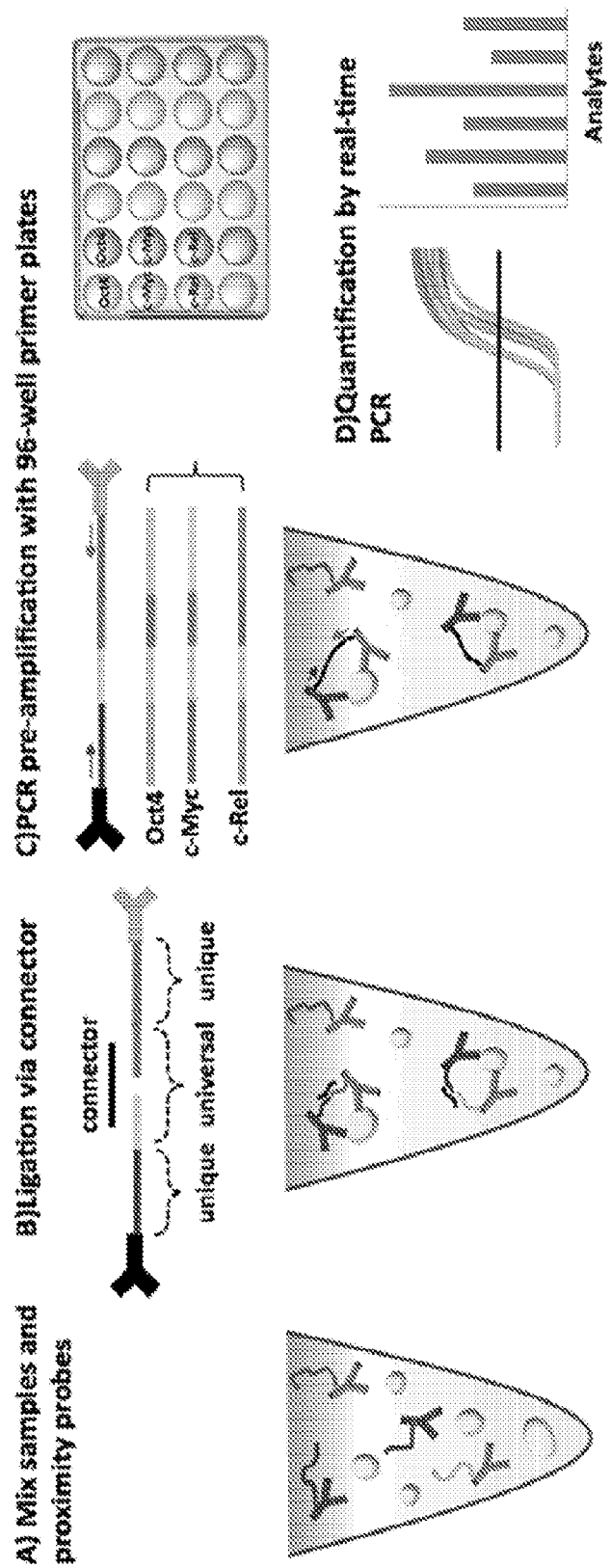
FIG. 7 depicts an exemplary workflow for a multiplexed Glyco-seq method to detect O-GlcNAcylation of transcription factors: (A) Mix "Click-it" labeled sample with proximity probes; (B) Ligation of DNA segments that are in close proximity via a universal connector and ligase; (C) Amplification of target specific amplicons by addition samples from (B) into 96-well primer plates; and (D) Quantification of the amplified product with real-time qPCR and analyze the signals.

This workflow is depicted in FIG. 7. (A) Mix "Click-it" labeled sample with proximity probes. (B) Ligation of DNA segments that are in close proximity via a universal connector and ligase. (C) Amplification of target specific amplicons by addition samples from (B) into 96-well primer plates. (D) Quantification of the amplified product with real-time qPCR and analyze the signals.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for detecting a glycosylated target protein in a sample, comprising:
   (a) contacting a sample comprising a probe-labeled glycosylated target protein with:
      (i) a first conjugate comprising a first nucleic acid tag linked to a first capture agent that specifically binds the target protein;
      (ii) a second conjugate comprising a second nucleic acid tag linked to a second capture agent that specifically binds the probe; and
      (iii) a bridging nucleic acid that hybridizes to the first and second nucleic acid tags;
   under conditions sufficient to specifically bind the first and second capture agents to the probe-labeled target protein and to hybridize the bridging nucleic acid to the first and second nucleic acid tags to produce a target protein-bound nucleic acid complex;
   (b) detecting the target protein-bound nucleic acid complex; and
   (c) determining the amount of total target protein in the sample.

2. The method of claim 1, wherein said determining is carried out using a proximity-based ligation assay comprising:
   (a) contacting the sample with:
      (i) a third conjugate comprising a third nucleic acid tag linked to a third capture agent that specifically binds a first epitope in the target protein;
      (ii) a fourth conjugate comprising a fourth nucleic acid tag linked to a fourth capture agent that specifically binds a second epitope in the target protein; and
      (iii) a bridging nucleic acid that hybridizes to the third and fourth nucleic acid tags;
   under conditions sufficient to specifically bind the third and fourth capture agents to the target protein and to hybridize the bridging nucleic acid to the third and fourth nucleic acid tags to produce a target protein-bound nucleic acid complex; and (b) detecting the target protein-bound nucleic acid complex.

3. The method of claim 1, comprising comparing the level of glycosylated target protein to the level of total target protein.

4. A composition, comprising:
(a) a first conjugate comprising a first nucleic acid tag linked to a first capture agent that is capable of specifically binding a target protein;
(b) a second conjugate comprising a second nucleic acid tag linked to a second capture agent that is capable of specifically binding a probe;
(c) a synthetic substrate comprising a sugar donor tagged with a first chemoselective tag;
(d) a reactive probe comprising a second chemoselective tag, wherein the second chemoselective tag is capable of reacting with the first chemoselective tag; and
(e) a third conjugate comprising a third nucleic acid tag linked to a third capture agent that specifically binds a first epitope in the target protein;
(f) a fourth conjugate comprising a fourth nucleic acid tag linked to a fourth capture agent that specifically binds a second epitope in the target protein;
(g) a first bridging nucleic acid that is complementary to the first and second nucleic acid tags; and
(h) a second bridging nucleic acid that is complementary to the third and fourth nucleic acid tags.

5. The composition of claim 4, wherein the first capture agent and the second capture agent are independently selected from a nucleic acid, an antibody, a protein, a peptide, or a small molecule.

6. The composition of claim 4, wherein the first capture agent is an anti-target protein antibody and the second capture agent is an anti-biotin antibody or an avidin moiety.

7. The composition of claim 4, wherein the composition further comprises a probe-labeled glycosylated target protein.

* * * * *